(12) United States Patent
Walker et al.

(10) Patent No.: US 6,890,942 B2
(45) Date of Patent: May 10, 2005

(54) ACYL SULFONAMIDES AS INHIBITORS OF HIV INTEGRASE

(75) Inventors: Michael A. Walker, Durham, CT (US); Hatice Belgin Gulgeze, Izmir (TR); Jacques Banville, St-Hubert (CA); Roger Remillard, Napierville (CA); Donald Corson, Annandale, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/839,661

(22) Filed: May 5, 2004

(65) Prior Publication Data
US 2005/0004232 A1 Jan. 6, 2005

Related U.S. Application Data
(60) Provisional application No. 60/471,033, filed on May 16, 2003.

(51) Int. Cl.⁷ .................. A61K 31/44; A61K 31/40; A61K 31/38; A61K 31/24; A61K 31/18
(52) U.S. Cl. .................. 514/346; 514/363; 514/380; 514/367; 514/369; 514/398; 514/407; 514/408; 514/445; 514/539; 514/562; 514/601; 514/603; 514/604; 514/605; 546/291; 548/139; 548/243; 548/187; 548/166; 548/338.1; 548/315.1; 548/567; 549/65; 560/13; 562/430; 564/86; 564/92; 564/99; 564/80
(58) Field of Search .................. 546/291, 65; 548/139, 548/243, 187, 166, 338.1, 315.1, 567; 560/13; 562/430; 564/86, 92, 99, 80; 514/346, 363, 367, 380, 369, 398, 407, 408, 445, 539, 562, 601, 603, 604, 605

(56) References Cited

U.S. PATENT DOCUMENTS

| 6,306,891 | B1 | * | 10/2001 | Selnick et al. | ............... 514/423 |
| 6,548,546 | B2 |   | 4/2003  | Walker et al.  |   |
| 2002/0123527 | A1 |   | 9/2002 | Walker et al.  |   |
| 2003/0027847 | A1 |   | 2/2003 | Walker et al.  |   |
| 2003/0176495 | A1 |   | 9/2003 | Walker et al.  |   |
| 2003/0181490 | A1 |   | 9/2003 | Walker et al.  |   |

* cited by examiner

Primary Examiner—Peter G. O'Sullivan
(74) Attorney, Agent, or Firm—James Epperson

(57) ABSTRACT

The present invention relates a series of compounds of Formula I

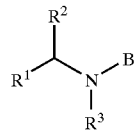

wherein $R^1$, $R^2$, $R^3$, and B are as defined in the specification. The compounds are useful for the inhibition of HIV integrase and for the treatment of AIDS or ARC by administering compounds of the formula.

13 Claims, No Drawings

ACYL SULFONAMIDES AS INHIBITORS OF HIV INTEGRASE

CROSS-REFERENCE TO RELATED APPLICATIONS

This application claims the benefit of U.S. provisional application 60/471,033, filed May 16, 2003.

BACKGROUND OF THE INVENTION

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics (UNAIDS: Report on the Global HIV/AIDS Epidemic, December 1998), indicate that as many as 33 million people worldwide are infected with the virus. In addition to the large number of individuals already infected, the virus continues to spread. Estimates from 1998 point to close to 6 million new infections in that year alone. In the same year there were approximately 2.5 million deaths associated with HIV and AIDS.

HIV expresses three enzymes, reverse transcriptase, an aspartyl protease and integrase, all of which are potential antiviral targets for the development of drugs for the treatment of AIDS. However, integrase stands out as being the only viral enzyme not targeted by current therapy. The integrase enzyme is responsible for insertion of the viral cDNA into the host cell genome, which is a critical step in the viral life cycle. There are a number of discrete steps involved in this process including processing of the viral cDNA by removal of two bases from each 3'-terminus and joining of the recessed ends to the host DNA. Studies have shown that in the absence of a functional integrase enzyme HIV is not infectious (Lafemina, R. L.; Schneider, C. L.; Robbins, H. L.; Callahan, P. L.; LeGrow, K.; Roth, E.; Emini, E. A. *J. Virol.* 1992, 66, 7414–7419 and Englund, G.; Theodore, T. S.; Freed, E.; Engelman, A.; Martin, M. A. *J. Virol.* 1995, 69, 3216–3219). Therefore, an inhibitor of integrase would be useful as a therapy for AIDS and HIV infection.

There are currently a number of antiviral drugs available to combat the infection. These drugs can be divided into three classes based on the viral protein they target and their mode of action. In particular, saquinavir, indinavir, ritonavir, nelfinavir and amprenavir are competitive inhibitors of the aspartyl protease expressed by HIV. Zidovudine, didanosine, stavudine, lamivudine, zalcitabine and abacavir are nucleoside reverse transcriptase inhibitors that behave as substrate mimics to halt viral cDNA synthesis. The non-nucleoside reverse transcriptase inhibitors, nevaripine, delavaridine and efavirenz inhibit the synthesis of viral cDNA via a non-competitive (or uncompetitive) mechanism. Used alone these drugs are effective in reducing viral replication. The effect is only temporary as the virus readily develops resistance to all known agents. However, combination therapy has proven very effective at both reducing virus and suppressing the emergence of resistance in a number of patients. In the US, where combination therapy is widely available, the number of HIV-related deaths has declined (Palella, F. J.; Delany, K. M.; Moorman, A. C.; Loveless, M. O.; Further, J.; Satten, G. A.; Aschman, D. J.; Holmberg, S. D. *N. Engl. J. Med.* 1998, 338, 853–860).

Unfortunately, not all patients are responsive and a large number fail this therapy. In fact, approximately 30–50% of patients ultimately fail combination therapy. Treatment failure in most cases is caused by the emergence of viral resistance. Viral resistance in turn is caused by the rapid turnover of HIV-1 during the course of infection combined with a high viral mutation rate. Under these circumstances incomplete viral suppression caused by insufficient drug potency, poor compliance to the complicated drug regiment as well as intrinsic pharmacological barriers to exposure provides fertile ground for resistance to emerge. More disturbing are recent findings which suggest that low-level replication continues even when viral plasma levels have dropped below detectable levels (<50 copies/ml) (Carpenter, C. C.; Cooper, D. A.; Fischl, M. A.; Gatell, J. M.; Gazzard, B. G.; Hammer, S. M.; Hirsch, M. S.; Jacobsen, D. M.; Katzenstein, D. A.; Montaner, J. S.; Richman, D. D.; Saag, M. S.; Schechter, M.; Schooley, R. T.; Thompson, M. A.; Vella, S.; Yeni, P. G.; Volberding, P. A. *JAMA* 2000, 283, 381–390). Clearly there is a need for new antiviral agents, preferably targeting other viral enzymes to reduce the rate of resistance and suppress viral replication even further.

Diketoacid and related HIV integrase inhibitors have been reported: Neamati, N. *Expert Opin. Ther. Patents,* 2002, 12 (5), 709–724; Walker et al. US patent application 2002/0027847; Katoh PCT application WO 03/016266. Nothing in these references teaches or suggests the novel compounds of this invention or their use as HIV integrase inhibitors.

SUMMARY OF INVENTION

The present invention relates to compounds of Formula I, or pharmaceutically acceptable salts, solvates or prodrugs thereof

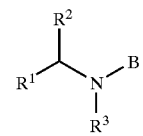

I wherein $R^1$, $R^2$, $R^3$, and B are defined below. These compounds function as inhibitors of HIV integrase. The present invention also includes pharmaceutical compositions useful for inhibiting HIV integrase or for treating patients infected with the HIV virus or suffering from AIDS or ARC (AIDS related complex), which comprises a therapeutically effective amount of one or more compounds of Formula I, including pharmaceutical acceptable salts, solvates or prodrugs thereof, and a pharmaceutically acceptable carrier.

The present invention also relates to a method of inhibiting HIV integrase by administering to a patient an effective amount of a compound of Formula I, or a pharmaceutically acceptable salt, solvate or prodrug thereof.

The present invention further relates to a method of treating patients infected by the HIV virus, or of treating AIDS or ARC, by administering to the patient an effective amount of a compound of Formula I, or a pharmaceutically acceptable salt, solvate or prodrug thereof.

The present invention further relates to a method of treating patients infected by the HIV virus, or of treating AIDS or ARC, by administering to the patient an effective amount of a compound of Formula I, or a pharmaceutically acceptable salt, solvate or prodrug thereof in conjunction with other known HIV or AIDS compounds.

DETAILED DESCRIPTION OF THE INVENTION

The present invention relates to compounds of Formula I, or pharmaceutically acceptable salts, solvates or prodrugs thereof

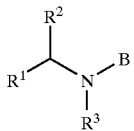
I wherein:
$R^1$ is
- -phenyl, or
- —$C_1$–$C_6$ alkyl-phenyl;

wherein phenyl is unsubstituted or substituted with 1–3 $R^4$;

$R^2$ is
- —H,
- —$C_1$–$C_6$ alkyl,
- -phenyl, or
- —$C_1$–$C_6$ alkyl phenyl;

wherein phenyl is unsubstituted or substituted with 1–3 $R^4$;

$R^3$ is
- —H,
- —$C_1$–$C_6$ alkyl, or
- —O—$C_1$–$C_6$ alkyl;

Each $R^4$ is independently selected from
- -halo,
- —$C_1$–$C_6$ alkyl,
- —$C_1$–$C_6$ haloalkyl,
- —$OR^5$, or
- —$CO_2R^5$;

Each $R^5$ is independently selected from
- —H or
- —$C_1$–$C_6$ alkyl;

B is selected from the group consisting of

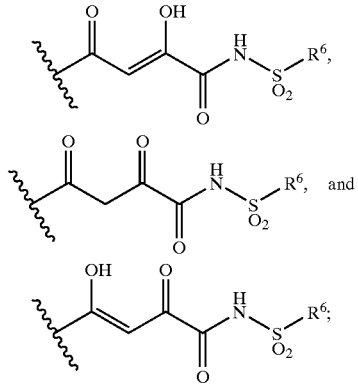

$R^6$ is
- —$C_1$–$C_6$ alkyl;
- —$C_3$–$C_7$ cycloalkyl;
- 1-($C_1$–$C_3$)alkylcyclopropyl;
- 1-benzylcyclopropyl;
- -tetrahydrothiophene 1,1-dioxoide;
- -phenyl, unsubstituted or substituted with 1–2 substituents selected from halo, —$C_1$–$C_6$ alkyl, —$C_1$–$C_6$ alkoxy, —$C_1$–$C_6$ carboalkoxy, —$C_1$–$C_6$ alkylamido, and N-[[(1-ethyl)pyrrolidin-2-yl]methyl]carboxamido; or
- -heteroaryl selected from the group consisting of thienyl, furanyl, pyrrolyl, pyridinyl, pyrimidinyl, pyridazinyl, oxadiazolyl, thiadiazolyl, isoxazolyl, imidazolyl, oxathiazolyl, oxathiazolyl, benzofuranyl, indolyl, benzoxazolyl, benzthiazolyl, thienyl, and pyrazolylthienyl moieties unsubstituted or substituted with 1–2 substituents selected from halo, —$C_1$–$C_6$ alkyl, —$C_1$–$C_2$ perhaloalkyl, —$C_1$–$C_6$ alkoxy, —$C_1$–$C_6$ carboalkoxy, and —$C_1$–$C_6$ alkylamido.

In the present invention, unless otherwise specified the following definitions apply.

The numbers in the subscript after the symbol "C" define the number of carbon atoms a particular group can contain. For example, "$C_1$–$C_6$" means a substituent containing from one to six carbon atoms.

As used herein, the term "alkyl" means a saturated, straight chain or branched monovalent hydrocarbon radical having the stated number of carbon atoms. Examples of such alkyl radicals include methyl, ethyl, n-propyl, isopropyl, n-butyl, isobutyl, sec-butyl, t-butyl and, where indicated, higher homologues and isomers such as n-pentyl, n-hexyl, 2-methylpentyl and the like. Haloalkyl refers to an alkyl radical that is substituted with one or more halo radicals, such as trifluoromethyl. Perhaloalkyl refers to an alkyl radical maximally substituted with halo radicals. For example, perfluoroethyl is pentafluoroethyl.

As used herein, the term "cycloalkyl" means a non-aromatic 3–6 membered ring. Examples include, cyclopropyl, cyclobutyl, cyclopentyl and cyclohexyl.

"Halo" means chloro, bromo, iodo or fluoro.

"Aryl" means an aromatic hydrocarbon having from six to ten carbon atoms; examples include phenyl and napthyl, indenyl, and azulenyl.

The term "heterocycle" refers to a monocyclic saturated heterocyclic nuclei having 3–6 atoms containing 1–3 heteroatoms selected from nitrogen, oxygen or sulfur. Heterocycles include, for example, piperidinyl, piperazinyl, pyrrolidinyl, thiazinyl and morpholinyl.

"Heteroaryl" means a five- or six-membered aromatic ring containing at least one and up to four non-carbon atoms selected from oxygen, sulfur and nitrogen. Examples of heteroaryl include 2-furyl, 3-furyl, 2-pyridyl, 3-pyridyl, 4-pyridyl, pyrazinyl, 2-thienyl, 3-thienyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, pyridazinyl, pyrimidinyl, 1,3,5-triazinyl and 1,3,5-trithianyl.

The invention includes all pharmaceutically acceptable salt forms of the instant compounds. Pharmaceutically acceptable salts are those in which the counter ions do not contribute significantly to the physiological activity or toxicity of the compounds and as such function as pharmacological equivalents. In many instances, salts have physical properties that make them desirable for formulation, such as solubility or crystallinity. The salts can be made according to common organic techniques employing commercially available reagents. Suitable anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Suitable cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

The invention also includes all solvated forms of the instant compounds, including hydrates. Solvates do not contribute significantly to the physiological activity or toxicity of the compounds and as such function as pharmacological equivalents. Solvates may form in stoichiometric amounts or may form with adventitious solvent or a combination of both. Some hydrated forms include monohydrate, hemihydrate, and dihydrate.

Certain compounds of Formula I may contain one or more chiral centers and exist in different optically active forms. When compounds of Formula I contain one chiral center, the compounds exist in two enantiomeric forms. The present invention includes both enantiomers and mixtures of enantiomers such as racemic mixtures. The enantiomers may be resolved by methods known to those skilled in the art, for example, by formation of diastereoisomeric salts which may be separated by crystallization, gas-liquid or liquid chromatography, selective reaction of one enantiomer with an enantiomer-specific reagent. It will be appreciated that where the desired enantiomer is converted into another chemical entity by a separation technique, then an additional step is required to form the desired enantiomeric form. Alternatively, specific enantiomers may be synthesized by asymmetric synthesis using optically active reagents, substrates, catalysts or solvents, or by converting one enantiomer into the other by asymmetric transformation.

The compounds of this invention can also exist as tautomers, as shown below; therefore the present invention also includes all tautomeric forms.

Some compounds of the invention include the following:
3-Hydroxy-4-oxo-4-(toluene-4-sulfonylamino)-but-2-enoic acid (4-fluoro-benzyl)-methoxy-amide;
3-Hydroxy-4-methanesulfonylamino-4-oxo-but-2-enoic acid (4-fluoro-benzyl)-methoxy-amide;
4-(5-Acetylamino-[1,3,4]thiadiazole-2-sulfonylamino)-3-hydroxy-4-oxo-but-2-enoic acid (4-fluoro-benzyl)-methoxy-amide;
4-Cyclobutylmethanesulfonylamino-3-hydroxy-4-oxo-but-2-enoic acid (4-fluoro-benzyl)-methoxy-amide;
4-Cyclohexanesulfonylamino-3-hydroxy-4-oxo-but-2-enoic acid (4-fluoro-benzyl)-methoxy-amide;
4-Cyclopentanesulfonylamino-3-hydroxy-4-oxo-but-2-enoic acid (4-fluoro-benzyl)-methoxy-amide;
4-Cyclopropanesulfonylamino-3-hydroxy-4-oxo-but-2-enoic acid (4-fluoro-benzyl)-methoxy-amide;
4-(3,5-Dimethyl-isoxazole-4-sulfonylamino)-3-hydroxy-4-oxo-but-2-enoic acid (4-fluoro-benzyl)-methoxy-amide;
3-Hydroxy-4-(6-methyl-pyridine-2-sulfonylamino)-4-oxo-but-2-enoic acid (4-fluoro-benzyl)-methoxy-amide;
4-(5-Chloro-thiophene-2-sulfonylamino)-3-hydroxy-4-oxo-but-2-enoic acid (4-fluoro-benzyl)-methoxy-amide;
4-(4-Acetylamino-benzenesulfonylamino)-3-hydroxy-4-oxo-but-2-enoic acid (4-fluoro-benzyl)-methoxy-amide;
4-(6-Ethoxy-benzothiazole-2-sulfonylamino)-3-hydroxy-4-oxo-but-2-enoic acid (4-fluoro-benzyl)-methoxy-amide;
4-(2,4-Dimethyl-thiazole-5-sulfonylamino)-3-hydroxy-4-oxo-but-2-enoic acid (4-fluoro-benzyl)-methoxy-amide;

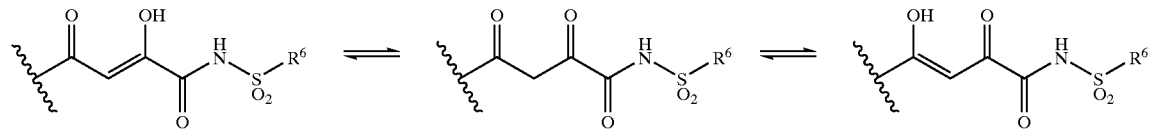

The term "therapeutically effective amount" means the total amount of each active component that is sufficient to show a meaningful benefit to the patient, e.g., halting or regression of the infection or slowing of the rate of infection. The term includes both single ingredients and combinations and the manner in which the components are administered.

The term "patient" includes humans as well as other mammals.

One aspect of the present invention is a compound of formula I wherein $R^1$ is phenyl substituted with 1–3 $R^4$ and $R^2$ is hydrogen.

Another aspect of the present invention is a compound of formula I wherein $R^1$ is —$(CH_2)_2$-phenyl where phenyl is substituted with 1–3 $R^4$, and $R^2$ is hydrogen.

Another aspect of the present invention is a compound of formula I wherein $R^6$ is —$C_1$–$C_6$ alkyl or —$C_3$–$C_7$ cycloalkyl.

Another aspect of the present invention is a compound of formula I wherein $R^6$ is -phenyl, unsubstituted or substituted with 1–2 substituents selected from halo, —$C_1$–$C_6$ alkyl, —$C_1$–$C_6$ alkoxy, —$C_1$–$C_6$ carboalkoxy, —$C_1$–$C_6$ alkylamido, and N-[(1-ethyl)pyrrolidin-2-yl]methyl] carboxamido.

Another aspect of the present invention is a compound of formula I wherein $R^6$ is heteroaryl selected from the group consisting of thienyl, furanyl, pyrrolyl, pyridinyl, pyrimidinyl, pyridazinyl, oxadiazolyl, thiadiazolyl, isoxazolyl, imidazolyl, oxathiazolyl, oxathiazolyl, benzofuranyl, indolyl, benzoxazolyl, benzthiazolyl, thienyl, and pyrazolylthienyl moieties unsubstituted or substituted with 1–2 substituents selected from halo, —$C_1$–$C_6$ alkyl, —$C_1$–$C_2$ perhaloalkyl, —$C_1$–$C_6$ alkoxy, —$C_1$–$C_6$ carboalkoxy, and —$C_1$–$C_6$ alkylamido.

3-Hydroxy-4-(1-methyl-1H-imidazole-4-sulfonylamino)-4-oxo-but-2-enoic acid (4-fluoro-benzyl)-methoxy-amide;
N-(1-Ethyl-pyrrolidin-2-ylmethyl)-5-{3-[(4-fluoro-benzyl)-methoxy-carbamoyl]-2-hydroxy-acryloylsulfamoyl}-2-methoxy-benz amide;
4-(1,1-Dioxo-tetrahydro-1λ$^6$-thiophene-3-sulfonylamino)-3-hydroxy-4-oxo-but-2-enoic acid (4-fluoro-benzyl)-methoxy-amide;
3-Hydroxy-4-[5-(1-methyl-5-trifluoromethyl-1H-pyrazol-3-yl)-thiophene-2-sulfonylamino]-4-oxo-but-2-enoic acid (4-fluoro-benzyl)-methoxy-amide;
3-Hydroxy-4-oxo-4-(1-propyl-cyclopropanesulfonylamino)-but-2-enoic acid (4-fluoro-benzyl)-methoxy-amide;
4-(1-Cyclopropylmethyl-cyclopropanesulfonylamino)-3-hydroxy-4-oxo-but-2-enoic acid (4-fluoro-benzyl)-methoxy-amide;
4-(1-Benzyl-cyclopropanesulfonylamino)-3-hydroxy-4-oxo-but-2-enoic acid (4-fluoro-benzyl)-methoxy-amide;
3-Hydroxy-4-methanesulfonylamino-4-oxo-but-2-enoic acid (4-fluoro-3-methyl-benzyl)-methoxy-amide;
3-Hydroxy-4-methanesulfonylamino-4-oxo-but-2-enoic acid (2-isopropoxy-benzyl)-methoxy-amide;
3-Hydroxy-4-methanesulfonylamino-4-oxo-but-2-enoic acid (3-fluoro-4-methyl-benzyl)-methoxy-amide;
3-Hydroxy-4-methanesulfonylamino-4-oxo-but-2-enoic acid[1-(4-fluoro-phenyl)-ethyl]-methoxy-amide;
3-Hydroxy-4-methanesulfonylamino-4-oxo-but-2-enoic acid (2-chloro-4-fluoro-benzyl)-methoxy-amide;
3-Hydroxy-4-methanesulfonylamino-4-oxo-but-2-enoic acid [1-(4-chloro-benzyl)-2-(4-chloro-phenyl)-ethyl]-methyl-amide; and 3-Hydroxy-4-methanesulfonylamino-4-oxo-but-2-enoic acid [3-(4-fluoro-phenyl)-propyl]-methoxy-amide.

General methods useful for the synthesis of compounds embodied in this invention are shown below. The preparations shown below are disclosed for the purpose of illustration and are not meant to be interpreted as limiting the processes to make the compounds by any other methods.

sodium hydride (NaH) or 1,8-diazabicyclo[5.4.0]undec-7-ene (DBU) to produce compounds of Formula I. Alternatively 1–3 can be hydrolyzed with NaOH or under similar conditions known to effect ester hydrolysis. The resulting intermediate, 1–4, can then be coupled to 1–5 using standard amide bond forming reagents such as those referenced in Pelletier, J. C; Hesson, D. P. Synlett (1995) 11, 1141–1142.

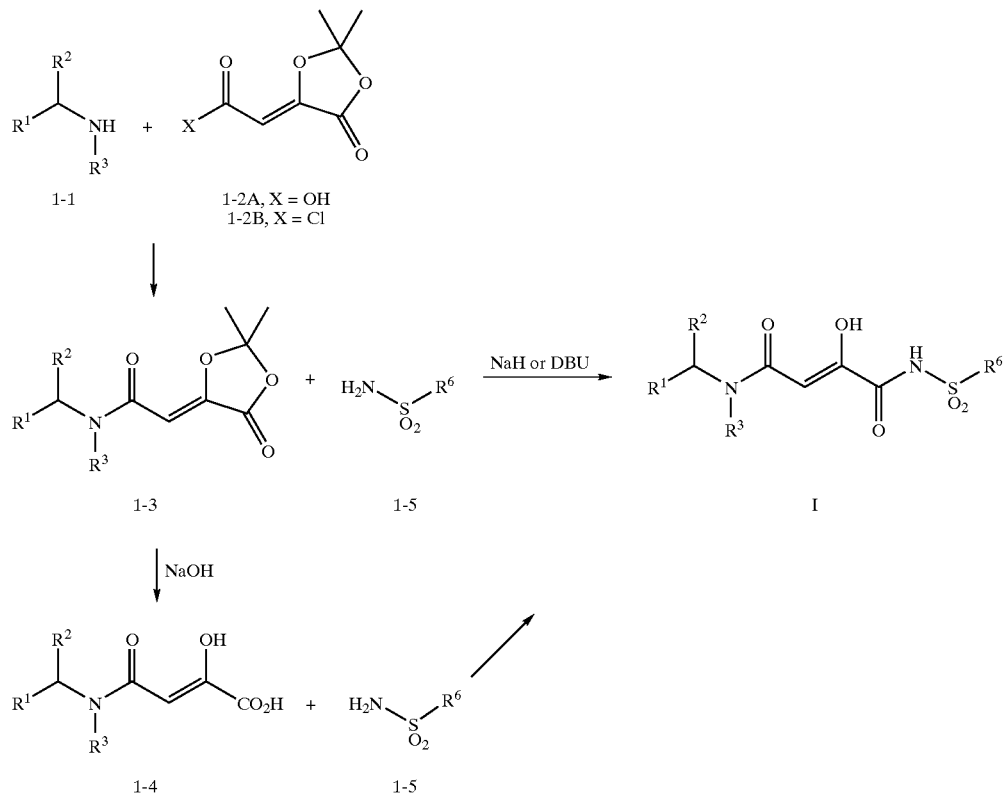

Scheme 1

It will be appreciated by those skilled in the art that a number of methods are available for the preparation of the compounds of the present invention as provided by Formula I. A compound of Formula I may be prepared by processes which include processes known in the chemical art for the production of structurally analogous compounds or by a novel process described herein. It will be recognized that it may be preferred or necessary to prepare a compound of Formula I in which a functional group is protected using a conventional protecting group, and then to remove the protecting group to provide the compound of Formula I.

Thus, there is provided a process for preparing a compound of Formula I (or a pharmaceutically acceptable salt, solvate, or prodrug thereof) as provided in any of the above descriptions or described in the examples, including the following.

The compounds of the present invention can be synthesized according to the scheme shown below. In scheme 1, amine 1-1 can be coupled with intermediate 1-2A or 1-2B using standard amide bond forming conditions and reagents such as those described in Jerry March, Advanced Organic Chemistry, 3$^{rd}$ edition, John Wiley & Sons, 1985 to generate intermediate amide 1–3. Intermediate 1–3 can be reacted with the sulfonamide 1–5 under basic conditions such as The compounds of Formula I demonstrate inhibition of HIV integrase as described in the specific embodiments section. Inhibition of HIV integrase can arrest or impede HIV infection. Therefore, the compounds of Formula I are useful for the the prevention or treatment of HIV infection and the treatment of consequent pathological conditions such as AIDS or ARC.

These therapeutic treatments generally employ pharmaceutical compositions. A pharmaceutical composition of the present invention comprises a therapeutically effective amount of a compound of Formula I in association with a pharmaceutically acceptable carrier, excipient or diluent. A therapeutically effective amount is the amount which produces a meaningful patient benefit. By "pharmaceutically acceptable" it is meant that the carrier, diluent or excipient is compatible with the other ingredients of the formulation and not deleterious to the recipient.

The present pharmaceutical compositions can be prepared by well known procedures using readily available ingredients. The compositions of this invention may be formulated so as to provide quick, sustained or delayed release of the compound of the invention, and optionally other active ingredients, after administration to the patient by employing procedures well known in the art. In making the compositions of the present invention, the active ingredients will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, beadlets, lozenges, sachets, elixirs, suspensions, emulsions, solutions, syrups, aerosols, (as a solid or in a liquid medium), soft and hard gelatin capsules, suppositories, sterile injectable solutions, sterile packaged powders and the like.

For oral administration, the compound is typically formulated with excipients such as binders, fillers, lubricants, extenders, diluents, disintegration agents and the like as are known in the art.

For parenteral administration, the compound is typically formulated in pharmaceutically acceptable non-toxic, parenterally-acceptable diluents or solvents, such as mannitol, 1,3-butanediol, water, 5 percent dextrose, Ringer's solution or isotonic sodium chloride solution, or suitable dispersing or wetting and suspending agents, such as sterile, bland, fixed oils, including synthetic mono- or diglycerides, and fatty acids, including oleic acid.

Typically, a compound of the present invention, or a salt, solvate, or prodrug thereof, can be formulated in unit dosage formulations comprising a dose between about 0.1 mg and about 1000 mg, or more, according to the particular treatment involved. An example of a unit dosage formulation comprises 5 mg of a compound of the present invention in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The treatment involves administering to a mammal in need of such treatment, a therapeutically effective amount of a compound of Formula I, or a pharmaceutically acceptable salt, solvate or prodrug thereof. Preferably, the compound is administered in the form of a pharmaceutical composition comprising a pharmaceutically acceptable carrier and a therapeutically effective amount of a compound of the present invention, or a pharmaceutically acceptable salt, solvate or prodrug thereof.

It will be appreciated by those skilled in the art that reference herein to treatment extends to prophylaxis as well as the treatment of established infections or symptoms. This includes initiating treatment pre- and post-exposure to the virus.

The compounds of the present invention may be administered orally, parenterally (including subcutaneous injections, intravenous, intramuscular, intrasternal injection or infusion techniques), by inhalation spray or rectally, in dosage unit formulations containing conventional non-toxic pharmaceutically acceptable carriers, adjuvants and vehicles.

When administered to humans, the compounds of the present invention are typically administered in a dosage range of 1 to 1000 mg/kg body weight in divided doses. One preferred dosage range is 1 to 200 mg/kg body weight orally in divided doses. It will be understood, however, that the specific dose level and frequency of dosage for any particular patient may be varied and will depend upon sound medical judgement.

In addition, the present invention can be administered in conjunction with other treatments for HIV, for example, HIV protease inhibitors, nucleoside reverse transcriptase inhibitors, non-nucleoside reverse transcriptase inhibitors, HIV-entry inhibitors, immunomodulators, antiinfectives, and vaccines.

Table 1 lists some agents useful in treating AIDS and HIV infection which are suitable for this invention.

TABLE 1

| Drug Name | Manufacturer | Indication |
|---|---|---|
| ANTIVIRALS | | |
| 097 (non-nucleoside reverse transcriptase inhibitor) | Hoechst/Bayer | HIV infection, AIDS, ARC |
| Amprenavir 141 W94 GW 141 (protease inhibitor) | Glaxo Wellcome | HIV infection, AIDS, ARC |
| Abacavir (1592U89) GW 1592 (RT inhibitor) | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection, ARC, PGL HIV positive, AIDS |
| Alpha Interferon HIV in combination w/Retrovir | Glaxo Wellcome | Kaposi's sarcoma |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) (protease inhibitor) | Bristol-Myers Squibb/ Novartis | HIV infection, AIDS, ARC |
| BMS-234475 (CGP-61755) (protease inhibitor) | Bristol-Myers Squibb/ Novartis | HIV infection, AIDS, ARC |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral, CMV retinitis |
| Delaviridine (RT inhibitor) | Pharmacia-Upjohn | HIV infection, AIDS, ARC |
| Dextran Sulfate | Ueno Fine Chem. Ind. Ltd. (Osaka, Japan) | AIDS, ARC, HIV positive asymptomatic |
| ddC Dideoxycytidine | Hoffman-La-Roche | HIV infection, AIDS, ARC |
| ddI Dideoxyinosine | Bristol-Myers Squibb | HIV infection, AIDS, ARC; combinationwith AZT/d4T |

TABLE 1-continued

| Drug Name | Manufacturer | Indication |
|---|---|---|
| DMP-450 (protease inhibitor) | AVID (Camden, NJ) | HIV infection, AIDS, ARC |
| Efavirenz (DMP 266) (-)6-Chloro-4-(S)-cyclopropylethynyl-4(S)-trifluoro-methyl-1,4-dihydro-2H-3,1-benzoxazin-2-one, STOCRINE (non-nucleoside RT inhibitor) | DuPont Merck | HIV infection, AIDS, ARC |
| EL10 | Elan Corp, PLC (Gainesville, GA) | HIV infection |
| Famciclovir | Smith Kline | herpes zoster, herpes simplex |
| FTC (reverse transcriptase inhibitor) | Emory University | HIV infection, AIDS, ARC |
| GS 840 (reverse transcriptase inhibitor) | Gilead | HIV infection, AIDS, ARC |
| HBY097 (non-nucleoside reverse transcriptase inhibitor) | Hoechst Marion Roussel | HIV infection, AIDS, ARC |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-associated diseases |
| Lamivudine, 3TC (reverse transcriptase inhibitor) | Glaxo Wellcome | HIV infection, AIDS, ARC, also with AZT |
| Lobucavir | Bristol-Myers Squibb | CMV infection |
| Nelfinavir (protease inhibitor) | Agouron Pharmaceuticals | HIV infection, AIDS, ARC |
| Nevirapine (RT inhibitor) | Boeheringer Ingleheim | HIV infection, AIDS, ARC |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 (protease inhibitor) | Pharmacia Upjohn | HIV infection, AIDS, ARC |
| Probucol | Vyrex | HIV infection, AIDS |
| RBC-CD4 | Sheffield Med. Tech (Houston, TX) | HIV infection, AIDS, ARC |
| Ritonavir (protease inhibitor) | Abbott | HIV infection, AIDS, ARC |
| Saquinavir (protease inhibitor) | Hoffmann-LaRoche | HIV infection, AIDS, ARC |
| Stavudine; d4T Didehydrodeoxy-thymidine | Bristol-Myers Squibb | HIV infection, AIDS, ARC |
| Valaciclovir | Glaxo Wellcome | Genital HSV & CMVinfections |
| Virazole Ribavirin | Viratek/ICN (Costa Mesa, CA) | asymptomatic HIV-positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) (reverse transcriptase inhibitor) | Gilead | HIV infection, AIDS |
| Combivir ® (reverse transcriptase inhibitor) | GSK | HIV infection, AIDS |
| abacavir succinate (or Ziagen ®) (reverse transcriptase inhibitor) | GSK | HIV infection, AIDS |
| Reyataz ® (atazanavir) | Bristol-Myers Squibb | HIV infection, AIDS |
| Fuzeon (Enfuvirtide, T-20) | Roche/Trimeris | HIV infection, AIDS, viral fusion inhibitor |
| Trizivir ® | | HIV infection, AIDS |
| Kaletra ® | Abbott | HIV infection, AIDS, ARC |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |

TABLE 1-continued

| Drug Name | Manufacturer | Indication |
|---|---|---|
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche in combination w/AZT | Kaposi's sarcoma, AIDS, ARC |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

DESCRIPTION OF SPECIFIC EMBODIMENTS

The specific examples that follow illustrate the syntheses of the compounds of the instant invention, and are not to be construed as limiting the invention in sphere or scope. The methods may be adapted to variations in order to produce compounds embraced by this invention but not specifically disclosed. Further, variations of the methods to produce the same compounds in somewhat different manner will also be evident to one skilled in the art.

In the following experimental procedures, all temperatures are understood to be in Centigrade (° C.) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs or br s), broad doublet (bd or br d), broad triplet (bt or br t), broad quartet (bq or br q), singlet (s), multiplet (m), doublet (d), quartet (q), triplet (t), doublet of doublet (dd), doublet of triplet (dt), and doublet of quartet (dq). The solvents employed for taking NMR spectra are acetone-$d_6$ (deuterated acetone), DMSO-$d_6$ (perdeuterodimethylsulfoxide), $D_2O$ (deuterated water), $CDCl_3$ (deuterochloroform) and other conventional deuterated solvents. The abbreviations used herein are American Chemical Society (ACS) or conventional abbreviations widely employed in the art. Some of which are: calcd (calculated); DMSO (dimethylsulfoxide); EtOAc (ethyl acetate); HPLC (high-pressure liquid chromatography); LC/MS (liquid chromatography, mass spectroscopy); LDA (lithium diisopropyl amide); LiHMDS (lithium bis(trimethylsilyl)amide); $SiO_2$ (silica gel); THF (tetrahydrofuran), TFA (trifluoroacetic acid), Me (methyl), Et (ethyl), Ph (phenyl), tBuOK (potassium tert-butoxide), NaOMe (sodium methoxide), NaOEt (sodium ethoxide), Boc (tert-butoxycarbonyl), and DEAD (diethylazo dicarboxylate).

The specific examples that follow illustrate the syntheses of the compounds of the instant invention, and are not to be construed as limiting the invention in sphere or scope. The methods may be adapted to variations in order to produce compounds embraced by this invention but not specifically disclosed. Further, variations of the methods to produce the same compounds in somewhat different manner will also be evident to one skilled in the art.

In the following experimental procedures, all temperatures are understood to be in Centigrade (C) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs or br s), broad doublet (bd or br d), broad triplet (bt or br t), broad quartet (bq or br q), singlet (s), multiplet (m), doublet (d), quartet (q), triplet (t), doublet of doublet (dd), doublet of triplet (dt), and doublet of quartet (dq). The solvents employed for taking NMR spectra are acetone-$d_6$ (deuterated acetone), DMSO-$d_6$ (perdeuterodimethylsulfoxide), $D_2O$ (deuterated water), $CDCl_3$ (deuterochloroform) and other conventional deuterated solvents.

Preparation of (2,2-Dimethyl-5-oxo-[1,3]dioxolan-4-ylidene)-acetic acid

Method A (S)-(+)-2,2-Dimethyl-5-oxo-1,3-dioxolane-4-acetic acid, tert-butyldiphenylsilyl ester

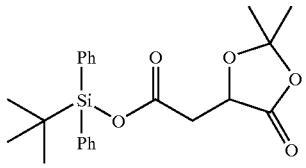

A solution of (S)-(+)-2,2-dimethyl-5-oxo-1,3-dioxolane-4-acetic acid (2.08 g, 11.9 mmol) in dry dichloromethane (20 ml) was treated with triethylamine (1.83 ml, 13.1 mmol)

followed by a solution of t-butylchlorodiphenylsilane (3.44 g, 12.5 mmol) in dichloromethane (5 ml) added dropwise over 5 minutes. After 3 hours at 22° C., the reaction mixture was diluted with toluene (250 ml) washed with water, saturated sodium bicarbonate, brine and dried over magnesium sulfate. Evaporation of the solvent under reduced pressure and chromatography of the residue on silica gel (4×12 cm) using a mixture of toluene and ethyl acetate (0–2%) as eluent gave 4.90 g (99% yield) of the title material as a clear oil. $^1$H NMR (400 MHz, CDCl$_3$) δ: 1.13 (s, 9), 1.58 (s, 3), 3.05 (m, 2), 4.79 (dd, 1, J=4, 7), 7.4–7.8 (m, 10).

4-Bromo-2,2-dimethyl-5-oxo-1,3-dioxolane-4-acetic acid, tert-butlydiphenylsilyl ester

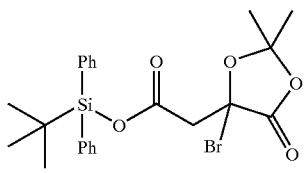

A solution of (S)-(+)-2,2-dimethyl-5-oxo-1,3-dioxolane-4-acetic acid, tert-butyldiphenylsilyl ester (21.65 g, 52.4 mmol) in carbon tetrachloride (160 ml) was treated with N-bromosuccinimide (9.35 g, 52.4 mmol) and 2,2'-azobisisobutyronitrile (200 mg) and the resulting mixture was heated under reflux (bath temperature 85° C.) while irradiating with a 500 watt lamp. After 10 minutes, the reaction mixture was cooled and the succinimide was filtered. The solvent was evaporated under vacuum to give the title bromide as a light yellow oil (~26 g) which was used immediately for the next step. $^1$H NMR (400 MHz, CDCl$_3$) δ: 1.12 (s, 9), 1.41 (s, 3), 1.80 (s, 3), 3.80 (m, 2), 7.3–7.7 (m, 10).

(Z)-2,2-Dimethyl-5-(tert-butyldiphenylsilyloxycarbonyl-methylene)-1,3-dioxolan-4-one

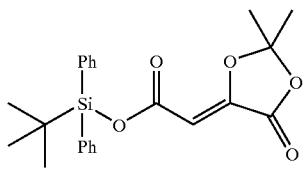

A solution of 4-bromo-2,2-dimethyl-5-oxo-1,3-dioxolane-4-acetic acid, tert-butyldiphenylsilyl ester (~26 g, 52.4 mmol) in dry tetrahydrofuran (160 ml) was cooled to 0° C. and treated dropwise over 5 minutes with 1,8-diazabicyclo [5,4,0] undec-7-ene (12.7 g, 78.8 mmol) and the resulting mixture was stirred at 5° C. for 1.5 hour. The solid formed was filtered and washed with a small amount of tetrahydrofuran. The filtrate was used as such for the next step.

Alternatively, the reaction mixture can be diluted with toluene, washed with water, saturated sodium bicarbonate, brine and dried (magnesium sulfate). Evaporation of the solvent gave an oil which was chromatographed on silica gel using a mixture of toluene and ethyl acetate (0–2%) as eluent. The title ester was obtained as an oil in 30–50% yield.

$^1$HNMR (400 MHz, CDCl$_3$) δ: 1.16 (s, 9), 1.76 (s, 6), 5.97 (s, 1), 7.4–7.8 (m, 10).

(2,2-Dimethyl-5-oxo-[1,3]dioxolan-4-ylidene)-acetic acid

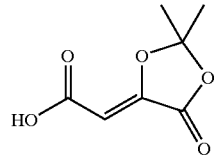

A solution of pure (Z)-2,2 dimethyl-5-(t-butyldiphenylsilyloxycarbonylmethylene)-1,3-dioxolan-4-one (2.80 g, 6.82 mmol) in tetrahydrofuran (40 ml) was treated at 22° C. with acetic acid (2 ml) followed by 6.8 ml of a 1 M solution of tetrabutylammonium fluoride in tetrahydrofuran. After 15 minutes at 22° C., the reaction mixture was diluted with ethyl acetate, washed with water, brine and dried (magnesium sulfate). The solvent was concentrated under reduced pressure and the residue was triturated with toluene to give 1.00 g (85% yield) of the title compound as a white crystalline material: mp 203–204° C. (dec.). IR (KBr) ν max (cm$^{-1}$): 1805, 1707 and 1662. $^1$H NMR (400 MHz, CDCl$_3$) δ: 1.78 (s, 6), 5.89 (s, 1). Anal. calcd for C$_7$H$_{8O5}$: C, 48.84; H, 4.68; Found: C, 48.84; H, 4.65.

Preparation of (2,2-Dimethyl-5-oxo-[1,3]dioxolan-4-ylidene)-acetic acid from crude (Z)-2,2-dimethyl-5-(tert-butyldiphenylsilyloxycarbonyl methylene)-1,3-dioxolan-4-one A solution of the crude (Z)-2,2-dimethyl-5-(tert-butyldiphenylsilyloxycarbonyl methylene)-1,3-dioxolan-4-one (52.4 mmol) in tetrahydrofuran (200 ml) was treated with acetic acid (13 ml) followed with 50 ml of a 1 M solution of tetrabutylammonium fluoride in tetrahydrofuran. After 15 minutes at 22° C., the reaction mixture was filtered and the filtrate was concentrated in vacuo. Trituration of the residue with toluene gave 6.3 g (70% yield for three steps) of the title material as a white solid (>95% pure by $^1$HNMR).

Method B (+)-2,2-Dimethyl-5-oxo-1,3-dioxolane-4-acetic acid, tert-butyldimethylsilyl ester

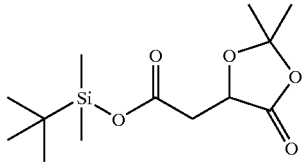

A solution of (S)-(+)-2,2-dimethyl-5-oxo-1,3-dioxolane-4-acetic acid (13.20 g, 75.8 mmol) in N,N-dimethylformamide (25 ml) was treated at 22° C. with imidazole (10.56 g, 0.155 mmol) followed by tert-butyldimethylsilyl chloride (12.0 g, 79.6 mmol) and the resulting mixture was stirred at 22° C. for 18 hours. The reaction mixture was then diluted with toluene (500 ml), washed with water (3 times), saturated sodium bicarbonate and brine. After drying (magnesium sulfate), the solvent was evaporated under reduced pressure to give an oil. Distillation under vacuum gave 20.9 g (96% yield) of the title material as a clear oil: Bp 80–90° C./0.1 torr (bulb to bulb distillation, air bath temperature). $^1$H NMR (400 MHz, CDCl$_3$) δ: 0.33 (s, 3), 0.36 (s, 3), 1.00 (s, 9), 1.11 (s, 3), 1.37 (s, 3), 2.72 (m, 2), 4.35 (dd, 1, J=4, 6).

4-Bromo-2,2-dimethyl-5-oxo-1,3-dioxolane-4-acetic acid, tert-butyldimethylsilyl ester

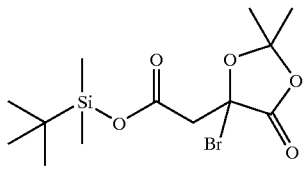

A solution of (S)-(+)-2,2-dimethyl-5-oxo-1,3-dioxolane4-acetic acid, t-butyldimethylsilyl ester (20.9 g, 72.4 mmol) in carbon tetrachloride (200 ml) was treated with N-bromosuccinimide (14.18 g, 79.6 mmol) and 2,2'-azobisisobutyronitrile (0.30 g) and the resulting mixture was heated under reflux while irradiating with a 500 W lamp. After ~5 minutes, a mild exothermic reaction was observed and the mixture was heated for an additional 5 minutes. The reaction mixture was then cooled in an ice bath and the floating succinimide was filtered and washed with a small amount of carbon tetrachloride. The filtrate was used immediately as such for the next step. $^1$H NMR (400 MHz, CDCl$_3$) δ: 0.27 (s, 3), 0.28 (s, 3), 0.94 (s, 9), 1.66 (s, 3), 1.84 (s, 3), 3.62 (m, 2).

(Z)-2,2-Dimethyl-5-(tert-butyldimethylsilyloxycarbonyl-methylene)-1,3-dioxolane

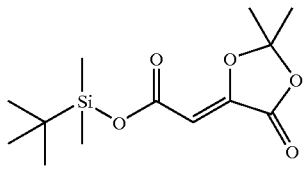

The solution of crude 4-bromo-2,2-dimethyl-5-oxo-1,3-dioxolane-4-acetic acid, tert-butyldimethylsilyl ester (72.4 mmol) in carbon tetrachloride (~220 ml) was cooled to 0–5° C. and treated dropwise over 10 minutes and under good stirring with a solution of 1,8-diazabicyclo (5,4,0) undec-7-ene (12.1 g, 79.6 mmol) in dry tetrahydrofuran (125 ml). A heavy precipitate was formed which gradually became a granular solid. After 1 h, the solid obtained was filtered and washed with a small amount of tetrahydrofuran. The filtrate was concentrated under reduced pressure to give a light orange oil which was used as such for the next step.

(2,2-Dimethyl-5-oxo-[1,3]dioxolan-4-ylidene)-acetic acid

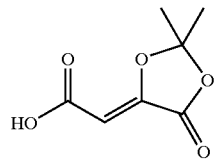

The crude (Z)-2,2-dimethyl-5-(tert-butyldimethylsilyloxycarbonylmethylene)-1,3-dioxolan-4-one (72.4 mmol) in tetrahydrofuran (50 ml) was treated at 22° C. with acetic acid (13 ml, 0.227 mmol) followed by 73 ml (73.0 mmol) of a 1M solution of tetrabutylammonium fluoride in tetrahydrofuran. After 1 h at 22° C., the reaction mixture was diluted with ethyl acetate (500 ml), washed with water, brine and dried (anhydrous magnesium sulfate). Evaporation of the solvent under reduced pressure and trituration of the residual solid with toluene (50 ml) gave 7.70 g (62% yield for 3 steps) of the title Z-isomer as a white crystalline solid. Concentration of the mother liquors yielded another 0.2 g of a 75:25 mixture of Z and E isomers. Z-Isomer; $^1$H NMR (400 MHz, CDCl$_3$) δ: 1.78 (s, 3), 5.89 (s, 1). E-Isomer: $^1$H NMR (400 MHz, CDCl$_3$) δ: 1.80 (s, 3), 6.03 (s, 1).

Preparation of (2,2-Dimethyl-5-oxo-[1,3]dioxolan-4-ylidene)-acetyl chloride

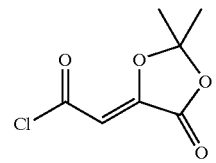

A mixture of (2,2-dimethyl-5-oxo-[1,3]dioxolan-4-ylidene)-acetic acid (0.50 g, 2.9 mmol) in dry dichloromethane (10 ml) was treated at 22° C. with oxalyl chloride (0.5 ml, 5.8 mmol) followed by a trace (capillary) of N,N-dimethylformamide. After 1 h at 22° C., the clear solution was concentrated in vacuo to give 0.55 g (quantitative) of the title acid chloride as a white crystalline solid.

Preparation of 4-Fluoro-benzaldehyde O-methyl-oxime

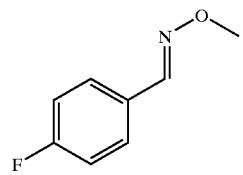

A solution of O-methyl-hydroxylamine, hydrochloride (13.4 g, 0.16 mol) in a mixture of water (150 ml) and tetrahydrofuran (50 ml) was treated with sodium acetate (11.2 g, 0.136 mol) followed by 4-fluorobenzaldehyde (11.57 g, 93.2 mmol) and the resulting mixture was stirred at 22° C. for 4 hours. The reaction mixture was then diluted with ether, washed with brine and dried over anhydrous magnesium sulfate. Evaporation of the solvent under reduced pressure gave 14.3 g of the crude title material as a clear oil which was used as such for the next step. Distillation of an aliquot in vacuo gave a clear oil; bp 45–50° C./0.5 torr. $^1$H NMR 400 MHz (CDCl$_3$) δ (ppm): 3.99 (3H, s), 7.09 (2H, m), 7.6 (2H, m), 8.06 (1H, s).

Preparation of N-(4-Fluoro-benzyl)-O-methyl-hydroxylamine

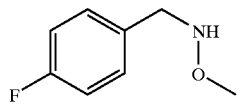

A solution of 4-fluorobenzaldehyde-O-methyloxime (93.2 mmol) in dichloromethane (150 ml) was treated with sodium cyanoborohydride (9.18 g, 0.146 mol) followed by 120 ml of 2 N hydrochloric acid in methanol added dropwise over 30 minutes. After 96 h at 22° C., the solvent was evaporated under reduced pressure, the residue was slurried with water and adjusted to pH 9 with 2 N aqueous sodium hydroxide. The aqueous phase was extracted twice with dichloromethane and the combined organic extracts were washed with brine, dried (magnesium sulfate) and concentrated under reduced pressure. The residual oil was chromatographed on silica gel (elution, toluene-ethyl acetate 0–10%) and gave 5.92 g (41% yield) of the title amine as a clear oil. $^1$H NMR 400 MHz (CDCl$_3$) δ (ppm): 3.49 (3H, s), 4.01 (2H, s), 5.69 (1H, broad s), 7.01 (2H, m), 7.31 (2H, m). The hydrochloride salt was obtained as a white solid: mp 170–171° C. Anal. calcd for C$_8$H$_{10}$FNO—HCl: C, 50.14; H, 5.78; N, 7.31. Found: C, 50.31; H, 5.80; N, 7.26

In an alternative procedure a solution of 4-fluorobenzaldehyde O-methyloxime (0.82 g, 5.35 mmol) in acetic acid (8 ml) was treated at 10° C. with sodium cyanoborohydride (0.67 g, 10.7 mmol) added in small portions over 10 min and the resulting solution was stirred at 25° C. for 18 h. The solvent was evaporated under reduce pressure (co-evaporation with toluene twice) and the residue was slurried with water and the pH was adjusted to 9 with 2 N aqueous sodium hydroxide. The aqueous phase was extracted twice with ether and the combined organic extracts were washed with brine, dried (magnesium sulfate) and concentrated under reduced pressure. The residual oil was chromatographed on silica gel (elution hexane-ethyl acetate, 8:2) and distilled in vacuo to give 0.62 g (75% yield) of the title amine as a clear oil.

Preparation of 2-(2,2-Dimethyl-5-oxo-[1,3]dioxolan-4-ylidene)-N-(4-fluoro-benzyl)-N-methoxy-acetamide

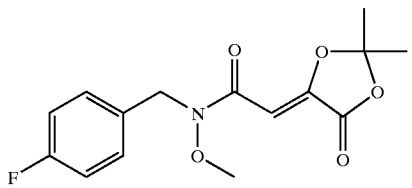

A solution of (2,2-dimethyl-5-oxo-[1,3]dioxolan-4-ylidene)-acetyl chloride, Compound 1-B, (2.45 g, 12.9 mmol) in dichloromethane (15 ml) was added dropwise over 10 minutes to a cold (0–5° C.) mixture of N-4-fluorobenzyl-O-methyl-hydroxylamine (2.0 g, 12.9 mmol) and pyridine (2.1 ml, 25.7 mmol) in dichloromethane (50 ml). The cooling bath was then removed and the solution was stirred at 22° C. for 30 minutes. The reaction mixture was then quenched by the addition of water and ethyl acetate. The organic phase was washed successively with 0.1 N hydrochloric acid, saturated sodium bicarbonate, brine and dried (magnesium sulfate). Evaporation of the solvent and chromatography of the residue on silica gel (toluene-ethyl acetate, 8:2) gave 3.72 g (93% yield) of the title amide as white crystals: mp 111° C. (ethyl acetate-hexane). $^1$H NMR 400 MHz (CDCl$_3$) δ (ppm): 1.75 (6H, s), 3.68 (3H, s), 4.79 (2H, s), 6.38 (1H, s), 7.0 (2H, m), 7.34 (2H, m). Anal. calcd for C$_{15}$H$_{16}$FNO$_5$: C, 58.25; H, 5.21; N, 4.52. Found: C, 58.33; H, 5.38; N, 4.51.

EXAMPLE 1

3-Hydroxy-4-oxo-4-(toluene-4-sulfonylamino)-but-2-enoic acid (4-fluoro-benzyl)-methoxy-amide

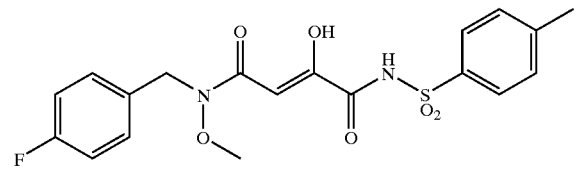

2-(2,2-Dimethyl-5-oxo-[1,3]dioxolan-4-ylidene)-N-(4-fluoro-benzyl)-N-methoxy-acetamide (309 mg, 1 mmol) and toluene-4-sulfonamide (171 mg, 1 mmol) were dissolved in 2 mL of THF. To this was added 40 mg of NaH (60% dispersion in mineral oil) and the resulting mixture stirred overnight. The reaction was quenched with 1N HCl and extracted with EtOAc. The organic layer was dried over Na$_2$SO$_4$, filtered and solvent removed to yield an oily solid. The product was triturated with MeOH to yield 80 mg solid (19% yield). HRMS (M–H) calcd for C$_{19}$H$_{18}$FN$_2$O$_6$S: 412.0870. Found: 421.0876. Anal calcd for C$_{19}$H$_{19}$FN$_2$O$_6$S: C, 54.02; H, 4.53; N, 6.63. Found: C, 54.07; H, 4.51; N, 6.51. $^1$H NMR (500 MHz, CDCl$_3$) δ: 2.44 (s, 3), 3.64 (s, 3), 4.76 (s, 2), 6.45 (s, 1), 7.03 (m, 2), 7.25 (m, 2), 7.35 (d, 2, J=8), 8.00 (d, 2, J=8), 9.11 (s, 1). $^{13}$C NMR (125 MHz, CDCl$_3$) δ: 21.68, 48.21, 63.07, 92.21, 115.67, 115.84, 128.70, 129.64, 130.18, 131.01, 135.14, 145.55, 158.85, 159.30, 161.60, 163.56, 170.87.

EXAMPLE 2

3-Hydroxy-4-methanesulfonylamino-4-oxo-but-2-enoic acid (4-fluoro-benzyl)-methoxy-amide

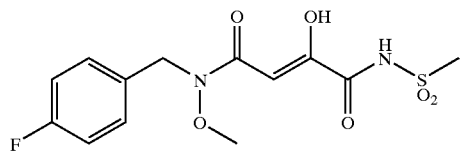

2-(2,2-Dimethyl-5-oxo-[1,3]dioxolan-4-ylidene)-N-(4-fluoro-benzyl)-N-methoxy-acetamide was treated with methane sulfonamide as described in the preparation of compound 1 to yield 100 mg solid (29% yield), mp=137° C. (decomposition). HRMS (M–H) cacld for C$_{13}$H$_{14}$FN$_2$O$_6$S: 345.056. Found: 345.0570. Anal calcd for C$_{13}$H$_{15}$FN$_2$O$_6$S: C, 45.08; H, 4.36; N, 8.08. Found: C, 45.20; H, 4.29; N, 7.92. $^1$H NMR (500 MHz, CDCl$_3$) δ: 3.36 (s, 3), 3.71 (s, 3), 4.81 (s, 2), 6.56 (s, 1), 7.04 (m, 2), 7.32 (m, 2), 8.97 (s, 1). $^{13}$C NMR (125 MHz, CDCl$_3$) δ: 41.60, 48.27, 63.16, 92.57, 115.65, 115.81, 130.19, 130.24, 130.97, 158.99, 160.05, 161.65, 163.61, 170.79.

EXAMPLE 3

4-(5-Acetylamino-[1,3,4]thiadiazole-2-sulfonylamino)-3-hydroxy-4-oxo-but-2-enoic acid (4-fluoro-benzyl)-methoxy-amide

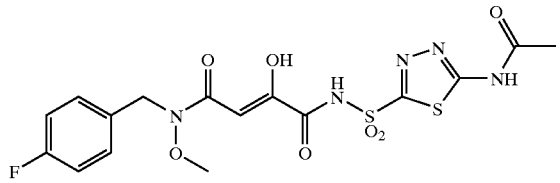

2-(2,2-Dimethyl-5-oxo-[1,3]dioxolan-4-ylidene)-N-(4-fluoro-benzyl)-N-methoxy-acetamide was treated with N-(5-sulfamoyl-[1,3,4]thiadiazol-2-yl)-acetamide as described in the preparation of compound 1 to yield the title compound. LCMS (M+H) calcd for $C_{16}H_{17}FN_5O_7S_2$: 474.1; found: 474.1. $^1$H NMR (500 MHz, DMSO) δ: 2.21 (s, 3), 3.62 (s, 3), 4.72 (s, 2), 6.32 (s, 1), 6.95 (m, 2), 7.22 (m, 2).

EXAMPLE 4

4-Cyclobutylmethanesulfonylamino-3-hydroxy4-oxo-but-2-enoic acid (4-fluoro-benzyl)-methoxy-amide

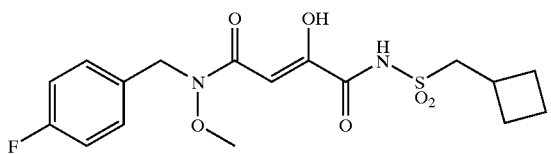

2-(2,2-Dimethyl-5-oxo-[1,3]dioxolan-4-ylidene)-N-(4-fluoro-benzyl)-N-methoxy-acetamide was treated with cyclobutyl-methanesulfonamide as described in the preparation of compound 1 to yield the title compound. LCMS (M+H) calcd for $C_{17}H_{22}FN_2O_6S$: 401.1; found: 401.0. $^1$H NMR (500 MHz, CDCl$_3$) δ: 1.87 (overlapping m, 3), 1.96 (m, 1), 2.21 (m, 2), 2.86 (heptet, 1, J=8), 3.55 (d, 2, J=7), 3.66 (s, 3), 4.79 (s, 2), 6.53 (s, 1), 7.02 (m, 2), 7.29 (m, 2). $^{13}$C NMR (125 MHz, CDCl$_3$) δ: 19.20, 28.12, 30.01, 48.31, 58.99, 63.23, 92.56, 115.72, 115.89, 130.28, 130.35, 131.05, 159.18, 160.12, 161.71, 163.67, 170.87.

EXAMPLE 5

4-Cyclohexanesulfonylamino-3-hydroxy-4-oxo-but-2-enoic acid (4-fluoro-benzyl)-methoxy-amide

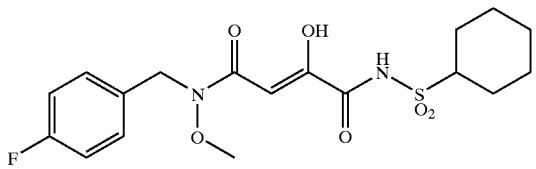

2-(2,2-Dimethyl-5-oxo-[1,3]dioxolan-4-ylidene)-N-(4-fluoro-benzyl)-N-methoxy-acetamide was treated with cyclohexanesulfonic acid amide as described in the preparation of compound 1 to yield the title compound. LCMS (M+H) calcd for $C_{18}H_{24}FN_2O_6S$: 415.1; found: 415.0. $^1$H NMR (500 MHz, CDCl$_3$) δ: 1.19 (overlapping m, 30,1.63 (overlapping m, 3), 1.90 (br m, 2), 2.17 (m, 2), 3.51 (m, 1), 3.69 (s, 3), 4.78 (s, 2), 6.53 (s, 1), 7.00 (m, 2), 7.26 (m, 2).

EXAMPLE 6

4-Cyclopentanesulfonylamino-3-hydroxy-4-oxo-but-2-enoic acid (4-fluoro-benzyl)-methoxy-amide

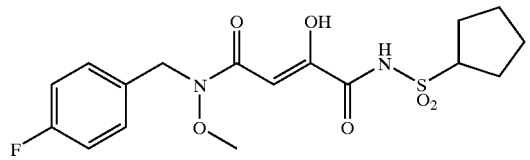

2-(2,2-Dimethyl-5-oxo-[1,3]dioxolan-4-ylidene)-N-(4-fluoro-benzyl)-N-methoxy-acetamide was treated with cyclopentanesulfonic acid amide as described in the preparation of compound 1 to yield the title compound. $^1$H NMR (500 MHz, CDCl$_3$) δ: 1.66 (m, 2), 1.83 (m, 2), 2.08 (overlapping m, 4), 3.69 (s, 3), 4.10 (p, 1, J=8), 4.79 (s, 2), 6.53 (s, 1), 7.01 (m, 2), 7.29 (m, 2), 8.84 (s, 1). $^{13}$C NMR (125 MHz, CDCl$_3$) δ: 20.55, 22.24, 42.90, 57.27, 57.80, 87.06, 110.29, 110.46, 124.85, 124.91, 125.66, 153.94, 154.50, 156.29, 158.25, 165.53.

EXAMPLE 7

4-Cyclopropanesulfonylamino-3-hydroxy-4-oxo-but-2-enoic acid (4-fluoro-benzyl)-methoxy-amide

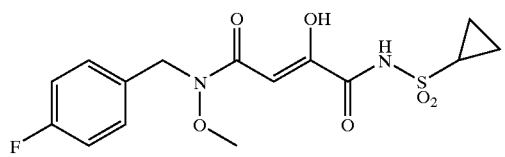

2-(2,2-Dimethyl-5-oxo-[1,3]dioxolan-4-ylidene)-N-(4-fluoro-benzyl)-N-methoxy-acetamide was treated with cyclopropanesulfonic acid amide as described in the preparation of compound 1 to yield the title compound. LCMS (M+H) calcd for $C_{15}H_{18}FN_2O_6S$: 373.1; found: 373.0. $^1$H NMR (500 MHz, CDCl$_3$) δ: 1.13 (m, 2), 1.44 (m, 2), 2.95 (m, 1), 3.68 (s, 3), 4.79 (s, 2), 6.55 (s, 1), 7.02 (m, 2), 7.29 (m, 2), 8.95 (s, 1). $^{13}$C NMR (125 MHz, CDCl$_3$) δ: 6.45, 31.41, 48.31, 63.22, 92.45, 115.71, 115.88, 130.25, 130.32, 131.09, 159.44, 159.74, 161.70, 163.67, 170.98.

EXAMPLE 8

4-(3,5-Dimethyl-isoxazole-4-sulfonylamino)-3-hydroxy-4-oxo-but-2-enoic acid (4-fluoro-benzyl)-methoxy-amide

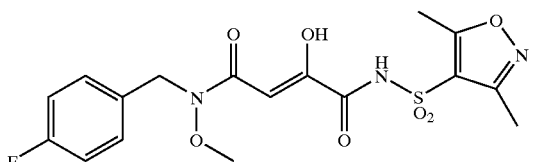

2-(2,2-Dimethyl-5-oxo-[1,3]dioxolan-4-ylidene)-N-(4-fluoro-benzyl)-N-methoxy-acetamide was treated with 3,5-dimethyl-isoxazole-4-sulfonic acid amide as described in the preparation of compound 1 to yield the title compound.

LCMS (M+H) calcd for $C_{17}H_{19}FN_3O_7S$: 428.1; found: 428.0. $^1$H NMR (500 MHz, CDCl$_3$) δ: 2.44 (s, 3), 2.75 (s, 3), 3.65 (s, 3), 4.77 (s, 2), 6.45 (s, 1), 7.01 (m, 2), 7.26 (m, 2). $^{13}$C NMR (125 MHz, CDCl$_3$) δ:10.83, 13.24, 48.33, 63.23, 92.57, 114.23, 115.71, 115.89, 130.19, 130.29, 130.96, 157.85, 158.89, 159.44, 161.71, 163.68, 170.81, 177.09.

EXAMPLE 9

3-Hydroxy-4-(6-methyl-pyridine-2-sulfonylamino)-4-oxo-but-2-enoic acid (4-fluoro-benzyl)-methoxy-amide

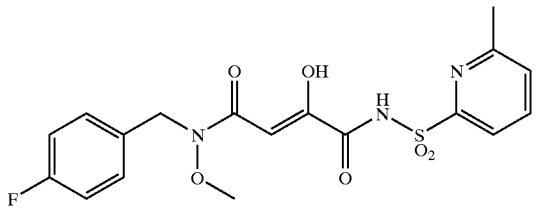

2-(2,2-Dimethyl-5-oxo-[1,3]dioxolan-4-ylidene)-N-(4-fluoro-benzyl)-N-methoxy-acetamide was treated with 6-methyl-pyridine-2-sulfonic acid amide as described in the preparation of compound 1 to yield the title compound. $^1$H NMR (500 MHz, CDCl$_3$) δ: 2.45 (s, 3), 3.61 (s, 3), 4.73 (s, 2), 6.38 (s, 1), 6.97 (m, 2), 7.23 (m, 2), 7.77 (m, 1), 8.17 (m, 1), 8.54 (s, 1). $^{13}$C NMR (125 MHz, CDCl$_3$) δ: 18.71, 48.22, 63.10, 92.48, 115.65, 115.82, 124.67, 130.24, 130.34, 131.09, 138.70, 139.36, 150.54, 152.19, 159.14, 161.66, 163.62, 170.80.

EXAMPLE 10

4-(5-Chloro-thiophene-2-sulfonylamino)-3-hydroxy-4-oxo-but-2-enoic acid (4-fluoro-benzyl)-methoxy-amide

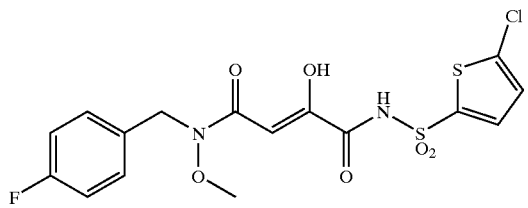

2-(2,2-Dimethyl-5-oxo-[1,3]dioxolan-4-ylidene)-N-(4-fluoro-benzyl)-N-methoxy-acetamide was treated with 5-chloro-thiophene-2-sulfonic acid amide as described in the preparation of compound 1 to yield the title compound. $^1$H NMR (500 MHz, CDCl$_3$) δ: 3.66 (s, 3), 4.77 (s, 2), 6.49 (s, 1), 7.00 (overlapping m, 3), 7.26 (m, 2), 7.72 (m, 1). $^{13}$C NMR (125 MHz, CDCl$_3$) δ: 48.29, 63.20, 92.61, 115.69, 115.87, 126.94, 130.23, 130.30, 131.01, 135.19, 135.85, 140.50, 159.01, 159.08, 161.69, 163.66, 170.84.

EXAMPLE 11

4-(4-Acetylamino-benzenesulfonylamino)-3-hydroxy-4-oxo-but-2-enoic acid (4-fluoro-benzyl)-methoxy-amide

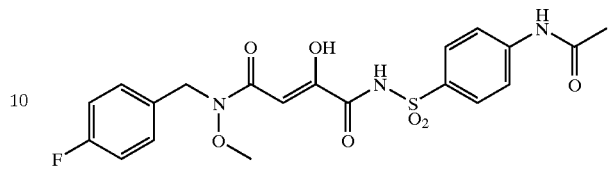

2-(2,2-Dimethyl-5-oxo-[1,3]dioxolan-4-ylidene)-N-(4-fluoro-benzyl)-N-methoxy-acetamide was treated with N-(4-sulfamoyl-phenyl)-acetamide as described in the preparation of compound 1 to yield the title compound. $^1$H NMR (500 MHz, DMSO) δ: 2.07 (s, 3), 3.60 (s, 3), 4.71 (s, 2), 6.26 (s, 1), 6.94 (m, 2), 7.21 (m, 2), 7.72 (m, 2), 7.86 (m, 2).

EXAMPLE 12

4-(6-Ethoxy-benzothiazole-2-sulfonylamino)-3-hydroxy-4-oxo-but-2-enoic acid (4-fluoro-benzyl)-methoxy-amide

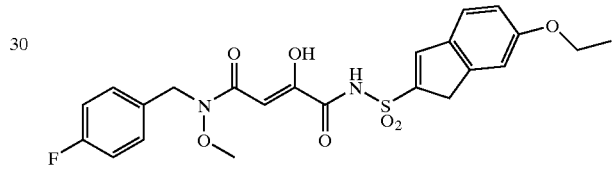

2-(2,2-Dimethyl-5-oxo-[1,3]dioxolan-4-ylidene)-N-(4-fluoro-benzyl)-N-methoxy-acetamide was treated with 6-ethoxy-benzothiazole-2-sulfonic acid amide as described in the preparation of compound 1 to yield the title compound. $^1$H NMR (500 MHz, CDCl$_3$) δ: 1.47 (t, 3, J=7), 3.62 (s, 3), 4.10 (q, 2, J=7), 4.75 (s, 2), 6.45 (s, 1), 7.02 (m, 2), 7.33–7.18 (overlapping m, 4), 8.05 (m, 1). $^{13}$C NMR (125 MHz, CDCl$_3$) δ: 14.69, 48.31, 63.18, 64.48, 92.87, 103.88, 115.69, 115.86, 118.94, 126.40, 130.24, 130.30, 131.00, 139.50, 146.56, 158.71, 159.16, 159.36, 159.59, 161.69, 163.65, 170.75.

EXAMPLE 13

4-(2,4-Dimethyl-thiazole-5-sulfonylamino)-3-hydroxy-4-oxo-but-2-enoic acid (4-fluoro-benzyl)-methoxy-amide

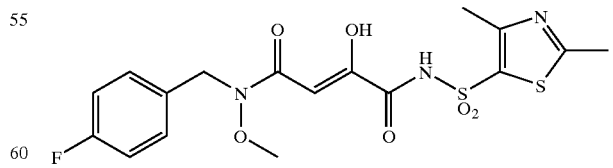

2-(2,2-Dimethyl-5-oxo-[1,3]dioxolan-4-ylidene)-N-(4-fluoro-benzyl)-N-methoxy-acetamide was treated with 2,4-dimethyl-thiazole-5-sulfonic acid amide as described in the preparation of compound 1 to yield the title compound. $^1$H NMR (500 MHz, CDCl$_3$) δ: 2.71 (s, 6), 3.63 (s, 3), 4.76 (s,

EXAMPLE 14

3-Hydroxy-4-(1-methyl-1H-imidazole-4-sulfonylamino)-4-oxo-but-2-enoic acid (4-fluoro-benzyl)-methoxy-amide

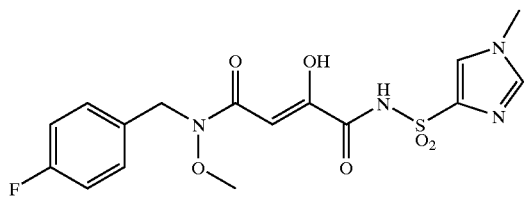

2-(2,2-Dimethyl-5-oxo-[1,3]dioxolan-4-ylidene)-N-(4-fluoro-benzyl)-N-methoxy-acetamide was treated with 1-methyl-1H-imidazole-4-sulfonic acid amide as described in the preparation of compound 1 to yield the title compound. $^1$H NMR (500 MHz, CDCl$_3$) δ: 3.63 (s, 3), 3.83 (s, 3), 4.75 (s, 2), 6.40 (s, 1), 7.02 (m, 2), 7.27 (m, 2), 7.74 (s, 1), 7.80 (s, 1). $^{13}$C NMR (125 MHz, CDCl$_3$) δ: 34.75, 48.21, 63.10, 92.33, 115.65, 115.82, 127.65, 130.24, 130.34, 131.11, 136.85, 139.42, 159.30, 159.55, 161.67, 163.63, 170.81.

EXAMPLE 15

N-(1-Ethyl-pyrrolidin-2-ylmethyl)-5-[3-[(4-fluoro-benzyl)-methoxy-carbamoyl]-2-hydroxy-acryloylsulfamoyl]-2-methoxy-benzamide

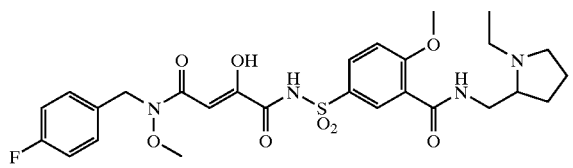

2-(2,2-Dimethyl-5-oxo-[1,3]dioxolan-4-ylidene)-N-(4-fluoro-benzyl)-N-methoxy-acetamide was treated with N-(1-ethyl-pyrrolidin-2-ylmethyl)-2-methoxy-5-sulfamoyl-benzamide as described in the preparation of compound 1 to yield the title compound. $^1$H NMR (500 MHz, CDCl$_3$) δ: 1.29 (t, 3, J=7), 1.86 (m, 1), 2.06 (m, 2), 2.26 (m, 1), 2.97 (m, 2), 3.50 (m, 1), 3.59 (s, 3), 3.64 (m, 1), 3.82 (m, 2), 3.95 (m, 1), 4.03 (s, 3), 4.72 (s, 2), 6.37 (s, 1), 6.95 (m, 2), 7.10 (m, 1), 7.23 (m, 2), 8.23 (m, 1), 8.71 (s, 1).

2), 6.47 (s, 1), 7.01 (m, 2), 7.26 (m, 2). $^{13}$C NMR (125 MHz, CDCl$_3$) δ: 16.51, 19.25, 48.29, 63.20, 92.66, 115.70, 115.87, 127.43, 130.23, 130.30, 130.97, 158.92, 159.24, 159.58, 161.69, 163.66, 170.81, 172.19.

EXAMPLE 16

4-(1,1-Dioxo-tetrahydro-1×6-thiophene-3-sulfonylamino)-3-hydroxy-4-oxo-but-2-enoic acid (4-fluoro-benzyl)-methoxy-amide

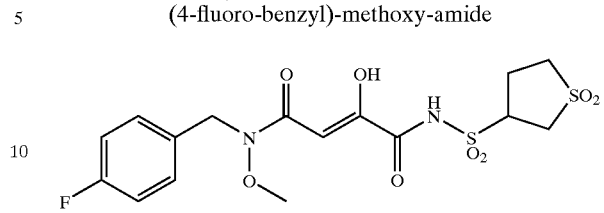

2-(2,2-Dimethyl-5-oxo-[1,3]dioxolan-4-ylidene)-N-(4-fluoro-benzyl)-N-methoxy-acetamide was treated with 1,1-dioxo-tetrahydro-1λ$^6$-thiophene-3-sulfonic acid amide as described in the preparation of compound 1 to yield the title compound. $^1$H NMR (500 MHz, CDCl$_3$) δ: 2.66 (m, 2), 3.16 (m, 1), 3.34 (m, 10, 3.48 (m, 2), 3.94 (s, 3), 4.51 (m, 1), 4.78 (s, 2), 6.52 (s, 1), 7.01 (m, 2), 7.28 (m, 2). $^{13}$C NMR (125 MHz, CDCl$_3$) δ: 22.89, 48.25, 49.91, 50.39, 57.43, 63.29, 93.24, 115.72, 115.90, 130.34, 130.95, 158.63, 160.50, 161.69, 163.65, 170.60.

EXAMPLE 17

3-Hydroxy-4-[5-(1-methyl-5-trifluoromethyl-1H-pyrazol-3-yl)-thiophene-2-sulfonylamino]-4-oxo-but-2-enoic acid (4-fluoro-benzyl)-methoxy-amide

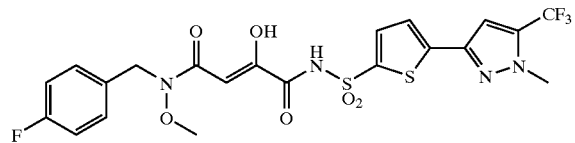

2-(2,2-Dimethyl-5-oxo-[1,3]dioxolan-4-ylidene)-N-(4-fluoro-benzyl)-N-methoxy-acetamide was treated with 5-(1-methyl-5-trifluoromethyl-1H-pyrazol-3-yl)-thiophene-2-sulfonic acid amide as described in the preparation of compound 1 to yield the title compound. $^1$H NMR (500 MHz, CDCl$_3$) δ: 3.66 (s, 3), 4.03 (s, 3), 4.76 (s, 2), 6.50 (s, 1), 6.71 (s, 1), 7.00 (m, 2), 7.20 (m, 1), 7.25 (m, 2), 7.93 (m, 1).

EXAMPLE 18

3-Hydroxy-4-oxo-4-(1-propyl-cyclopropanesulfonylamino)-but-2-enoic acid (4-fluoro-benzyl)-methoxy-amide

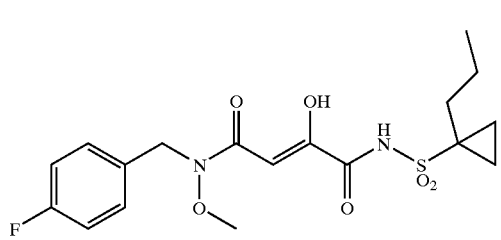

2-(2,2-Dimethyl-5-oxo-[1,3]dioxolan-4-ylidene)-N-(4-fluoro-benzyl)-N-methoxy-acetamide was treated with 1-propyl-cyclopropanesulfonic acid amide as described in the preparation of compound 1 to yield the title compound.

MS (M–H) calcd for C$_{18}$H$_{22}$FN$_2$O$_6$S: 413.1. Found: 413.0. $^1$H NMR (500 MHz, CDCl$_3$) δ: 0.92 (t, 3, J=8), 1.00 (m, 2), 1.54 (m, 2), 1.74 (m, 2), 1.84 (m, 2), 3.68 (s, 3), 4.79 (s, 2), 6.54 (s, 1), 7.04 (m, 2), 7.29 (m, 2), 8.79 (s, 1). Anal calcd for C$_{18}$H$_{23}$FN$_2$O$_6$S: C, 52.16; H, 5.59; N, 6.76. Found: C, 52.20; H, 5.69; N, 6.66.

EXAMPLE 19

4-(1-Cyclopropylmethyl-cyclopropanesulfonylamino)-3-hydroxy-4-oxo-but-2-enoic acid (4-fluoro-benzyl)-methoxy-amide

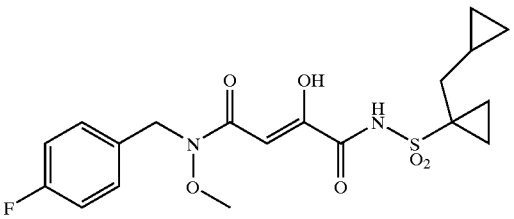

2-(2,2-Dimethyl-5-oxo-[1,3]dioxolan-4-ylidene)-N-(4-fluoro-benzyl)-N-methoxy-acetamide was treated with 1-cyclopropylmethyl-cyclopropanesulfonic acid amide as described in the preparation of compound 1 to yield the title compound. MS (M–H) calcd for C$_{19}$H$_{22}$FN$_2$O$_6$S: 425.1. Found: 425.0. $^1$H NMR (500 MHz, CDCl$_3$) δ: 0.12 (m, 2), 0.50 (m, 2), 0.70 (m, 1), 1.14 (m, 2), 1.75 (m, 2), 1.88 (m, 2), 3.69 (s, 3), 4.79 (s, 2), 6.54 (s, 1), 7.03 (m, 2), 7.30 (m, 2), 8.83 (s, 1). Anal calcd for C$_{19}$H$_{23}$FN$_2$O$_6$S; C, 53.51; H, 5.43; N, 6.56. Found: C, 53.43; H, 5.64; N, 6.51.

EXAMPLE 20

4-(1-Benzyl-cyclopropanesulfonylamino)-3-hydroxy-4-oxo-but-2-enoic acid (4-fluoro-benzyl)-methoxy-amide

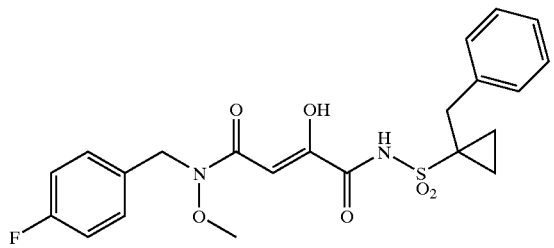

2-(2,2-Dimethyl-5-oxo-[1,3]dioxolan-4-ylidene)-N-(4-fluoro-benzyl)-N-methoxy-acetamide was treated with 1-benzyl-cyclopropanesulfonic acid amide as described in the preparation of compound 1 to yield the title compound. MS (M–H) calcd for C$_{22}$H$_{22}$FN$_2$O$_6$S: 461.1. Found: 461.2. HRMS (M+H) calcd for C$_{22}$H$_{24}$FN$_2$O$_6$S: 463.1339. Found: 463.1331. $^1$H NMR (500 MHz, CDCl$_3$) 0.95 (m, 2), 1.26 (m, 2), 3.25 (s, 2), 3.85 (s, 3), 4.79 (s, 2), 6.43 (s, 1), 7.06–7.32 (overlapping m, 9). Anal calcd for C$_{22}$H$_{23}$FN$_2$O$_6$S: C, 57.13; H, 5.01; N, 6.05. Found: C, 56.06; H, 5.42; N, 6.25.

Preparation of 4-Formyl-benzoic acid tert-butyl ester

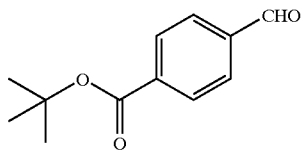

A suspension of 4-carboxybenzaldehyde (5.2 g, 34.6 mmol) in tetrahydrofuran (130 ml) was treated under argon with di-tert-butyl dicarbonate (15.3 g, 70.0 mmol) and 4-dimethylaminopyridine (1.28 g, 10.0 mmol) and the resulting mixture was stirred at 22° C. for 72 h. After dilution with dichloromethane, the reaction mixture was washed successively with 5% citric acid, saturated sodium bicarbonate and brine and dried over anhydrous magnesium sulphate. Evaporation of the solvent under reduced pressure and chromatography of the residue on silica gel (elution toluene-ethyl acetate, 95:5) yielded 2.43 g (34% yield) of the title ester as a white solid. $^1$HNMR 400 MHz (CDCl$_3$) δ (ppm): 1.61 (9H, s, t-Bu), 7.92 (2H, d, J=8.3 Hz, aromatics), 8.13 (2H, d, J=8.3 Hz, aromatics), 10.09 (1H, s, CH).

Preparation of 4-(Methoxyimino-methyl)-benzoic acid tert-butyl ester

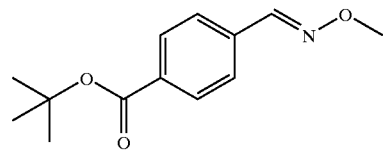

Reaction of 4-formyl-benzoic acid tert-butyl ester with methoxylamine hydrochloride as described in the preparation of compound 1-A gave the title oxime ether as a clear oil after chromatography on silica gel (elution hexane-ethyl acetate, 96:4) (79% yield). $^1$HNMR 400 MHz (CDCl$_3$) δ (ppm): 1.60 (9H, s, t-Bu), 4.00 (3H, s, OCH$_3$), 7.62 (2H, d, J=8.0 Hz, aromatics), 7.97 (2H, d, J=8.0 Hz, aromatics), 8.08 (1H, s, CH).

Preparation of 4-(Methoxyamino-methyl)-benzoic acid tert-butyl ester

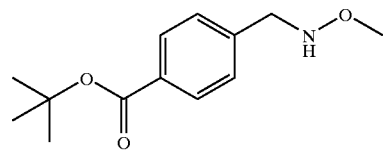

Reduction of 4-(methoxyimino-methyl)-benzoic acid tert-butyl ester with sodium cyanoborohydride as described in the preparation of compound 1-B gave the title hydroxylamine as a clear oil after chromatography on silica gel (elution hexane-ethyl acetate 8:2) (56% yield). $^1$HNMR 400 MHz (CDCl$_3$) δ (ppm): 1.59 (9H, s, t-Bu), 3.49 (3H, s, OCH$_3$), 4.09 (2H, s, NCH$_2$), 7.41 (2H, d, J=8.6 Hz, aromatics), 7.96 (2H, d, J=8.6 Hz, aromatics). The hydro chloride salt was obtained as a white solid: mp 130–132° C. Anal. calcd for C$_{13}$H$_{19}$NO$_3$—HCl: C, 57.04; H, 7.36; N, 5.12. Found: C, 56.90; H, 7.27; N, 5.00.

Preparation of 4-({[2-(2,2-Dimethyl-5-oxo-[1,3]dioxolan-4-ylidene)-acetyl]-methoxy-amino}-methyl)-benzoic acid tert-butyl ester

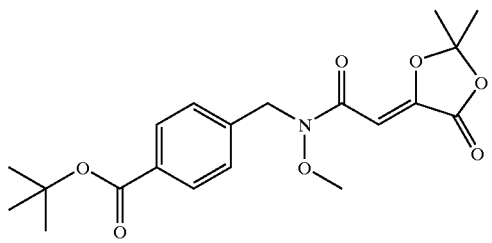

Reaction of (2,2-dimethyl-5-oxo-[1,3]dioxolan-4-ylidene)-acetyl chloride with 4-(methoxyamino-methyl)-benzoic acid tert-butyl ester as described in the preparation of compound 1-C gave the title amide as white crystals (93% yield): mp 137–138° C. (dichloromethane-hexane). $^1$HNMR 400 MHz (CDCl$_3$) δ (ppm): 1.58 (9H, s, t-Bu), 1.76 (6H, s, CH$_3$), 3.67 (3H, s, OCH$_3$), 4.87 (2H, s, NCH$_2$), 6.40 (1H, s, CH), 7.39 (2H, d, J=8.2 Hz, aromatics), 7.95 (2H, d, J=8.2 Hz, aromatics). Anal. calcd for C$_{20}$H$_{25}$NO$_7$: C, 61.37; H, 6.44; N, 3.58. Found: C, 61.23; H, 6.25; N, 3.52.

Preparation of 4-({[2-(2,2-Dimethyl-5-oxo-[1,3]dioxolan-4-ylidene)-acetyl]-methoxy-amino}-methyl)-benzoic acid

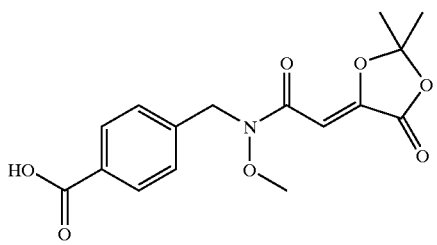

A solution of 4-({[2-(2,2-dimethyl-5-oxo-[1,3]dioxolan-4-ylidene)-acetyl]-methoxy-amino}-methyl)-benzoic acid tert-butyl ester (0.60 g, 1.53 mmol) in dichloromethane (25 ml) was treated at 22° C. with trifluoroacetic acid (6 ml) and the resulting mixture was stirred for 1 h. Evaporation of the solvent in vacuo and recrystallization of the solid residue gave 0.457 g (89% yield) of the title material as white crystals: mp 217–219° C. (dichloromethane-hexane). $^1$HNMR 400 MHz (DMSO-d$_6$) δ (ppm): 1.70 (6H, s, CH$_3$), 3.72 (2H, s, OCH$_3$), 4.89 (2H, s, NCH$_2$), 6.18 (1H, s, CH), 7.39 (2H, d, J=8.3 Hz, aromatics), 7.91 (2H, d, J=8.3 Hz, aromatics), 12.9 (1H, broad s, OH). Anal. calcd for C$_{16}$H$_{17}$NO$_7$: C, 57.31; H, 5.11; N, 4.18. Found: C, 57.33; H, 5.08; N, 4.25.

EXAMPLE 21

4-{[(3-Hydroxy-4-methanesulfonylamino-4-oxo-but-2-enoyl)-methoxy-amino]-methyl}-benzoic acid

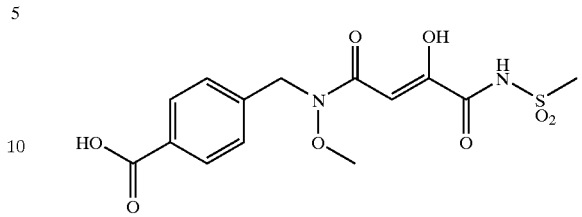

Reaction of 4-({[2-(2,2-dimethyl-5-oxo-[1,3]dioxolan-4-ylidene)-acetyl]-methoxy-amino}-methyl)-benzoic acid (0.125 g, 0.37 mmol) with methanesulfonamide (0.053 g, 0.55 mmol) as described for compound 1 gave 0.131 g (95%) of the title amide as a white solid after recrystallization from acetonitrile; mp 119–124° C. $^1$H NMR (400 MHz, DMSO) δ: (ppm)); mixture of rotamers: 2.99 and 3.09 (3H, 2 S, SO$_2$CH$_3$), 3.42 and 3.54 (3H, 2 s, OCH$_3$), 4.63 and 4.76 (2H, 2 s, NCH$_2$), 6.14 (1H, s, CH), 7.17 (2H, m, aromatics), 7.69 (2H, m, aromatics). HRMS (ESI/pos) calculated for C$_{14}$H$_{17}$N$_2$O$_8$S, [M+H]$^+$: 373.070563; found: 373.070061. Anal. calcd for C$_{14}$H$_{16}$N$_2$O$_8$S: C, 45.16; H, 4.33; N, 7.52; found: C, 45.22; H, 4.70; N, 8.12.

Preparation of 4-Fluoro-3-methyl-benzaldehyde O-methyl-oxime

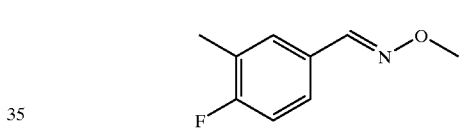

Reaction of 4-fluoro-3-methyl-benzaldehyde with methoxylamine hydrochloride as described in the preparation of compound 1-A gave the title oxime ether as a clear oil after chromatography on silica gel (elution hexane-ethyl acetate 8:2) (100% yield). $^1$HNMR indicated a 9:1 mixture of E- and Z-isomers. $^1$HNMR 400 MHz (CDCl$_3$) δ (ppm): (E-isomer) 2.29 (3H, broad s, CH$_3$), 3.96 (3H, s, OCH$_3$), 7.0 (1H, m, aromatic), 7.34 (1H, m, aromatic), 7.4 (1H, m, aromatic), 8.0 (1H, s, CH).

Preparation of N-(4-Fluoro-3-methyl-benzyl)-O-methyl-hydroxylamine

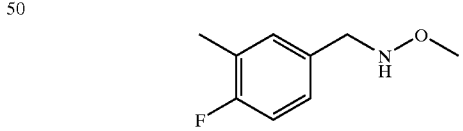

Reduction of 4-fluoro-3-methyl-benzaldehyde O-methyloxime with sodium cyanoborohydride as described in the preparation of compound 1-B gave the title hydroxylamine as a clear oil after chromatography on silica gel (elution hexane-ethyl acetate 8: 2) (94% yield). $^1$HNMR 400 MHz (CDCl$_3$) δ (ppm): 2.27 (3H, broad s, CH$_3$), 3.50 (3H, s, OCH$_3$), 3.97 (2H, broad s, NCH$_2$), 5.67 (1H, broad, NH), 6.95 (1H, m, aromatic), 7.11–7.17 (2H, m, aromatics). The hydrochloride salt was obtained as a white solid: mp 162° C. Anal. calcd for C$_9$H$_{12}$FNO—HCl: C, 52.56; H, 6.37; N, 6.81. Found: C, 52.80; H, 6.33; N, 6.70.

Preparation of 2-(2,2-Dimethyl-5-oxo-[1,3]
dioxolan-4-ylidene)-N-(4-Fluoro-3-methyl-benzyl)-
N-methoxy-acetamide

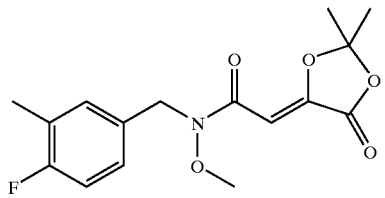

Reaction of (2,2-dimethyl-5-oxo-[1,3]dioxolan-4-ylidene)-acetyl chloride with N-(4-fluoro-3-methyl-benzyl)-O-methyl-hydroxylamine as described in the preparation of compound 1-C gave the title amide as white crystals (95% yield): mp 107–108° C. (ethyl acetate-hexane). $^1$HNMR 400 MHz (CDCl$_3$) δ (ppm): 1.75 (6H, s, CH$_3$), 2.26 (3H, broad s, CH$_3$), 3.69 (3H, s, OCH$_3$), 4.75 (2H, s, NCH$_2$), 6.39 (1H, s, CH), 6.95 (1H, m, aromatic), 7.13–7.19 (2H, m, aromatics). Anal. calcd for C$_{16}$H$_{18}$FNO$_5$: C, 59.43; H, 5.61; N, 4.33. Found: C, 59.24; H, 5.47; N 4.29.

EXAMPLE 22

3-Hydroxy-4-methanesulfonylamino-4-oxo-but-2-enoic acid (4-fluoro-3-methyl-benzyl)-methoxy-amide

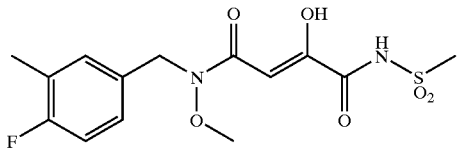

A solution of 2-(2,2-dimethyl-5-oxo-[1,3]dioxolan-4-ylidene)-N-(4-fluoro-3-methyl-benzyl)-N-methoxy-acetamide (0.320 g, 0.99 mmol) and methanesulfonamide (0.095 g, 1.0 mmol) in N,N-dimethylformamide (2 ml) was treated at 22° C. with sodium hydride (0.080 g of a 60% dispersion in mineral oil, 2.0 mmol) added in small portions over 5 min. After 1 h, the reaction mixture was quenched by the addition of 2 N aqueous hydrochloric acid and ethyl acetate. The organic phase was washed with brine and dried over anhydrous magnesium sulfate. Evaporation of the solvent and crystallization of the residue from ethyl acetate and hexane gave 0.244 g (68% yield) of compound 23 as a white solid; mp=138° C. (decomposition). $^1$H NMR (400 MHz, CDCl$_3$) δ: 2.27 (3H, d, J=1.9 Hz, CH$_3$), 3.36 (3H, s, CH$_3$), 3.70 (3H, s, CH$_3$), 4.76 (2H, s, NCH$_2$), 6.56 (1H, s, CH), 6.95–7.14 (3H, m, aromatics), 8.96 (1H, broad s, NH). Anal. calcd for C$_{14}$H$_{17}$FN$_2$O$_6$S: C, 46.66; H, 4.75; N, 7.77; found: C, 46.76; H, 4.74; N, 7.64.

Preparation of 2-Isopropoxy-benzaldehyde O-methyloxime

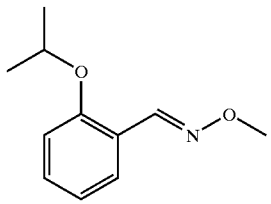

Reaction of 2-isopropoxybenzaldehyde (Hach, Collect. Czech. Commun., 23, 1958, 1902–1907) with methoxylamine hydrochloride as described in the preparation of compound 1-A gave the title oxime ether as a clear oil after chromatography on silica gel (elution hexane-ethyl acetate 8:2) (96% yield). $^1$HNMR indicated a 95:5 mixture of E- and Z-isomers. $^1$HNMR 400 MHz (CDCl$_3$) δ (ppm): (E-isomer) 1.33 (6H, d, J=6.1 Hz, CH$_3$), 3.97 (3H, s, OCH$_3$), 4.56 (1H, m, CH), 6.90 (2H, m, aromatics), 7.30 (1H, m, aromatic), 7.79 (1H, dd, J=2.0 Hz and J=7.6 Hz, aromatic), 8.47 (1H, s, CH).

Preparation of N-(2-Isopropoxy-benzyl)-O-methyl-hydroxylamine

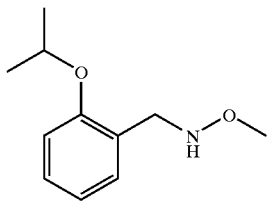

Reduction of 2-isopropoxy-benzaldehyde O-methyloxime with sodium cyanoborohydride as described in the preparation of compound 1-B gave the title hydroxylamine as a clear oil after chromatography on silica gel (elution hexane-ethyl acetate 8:2) (83% yield). $^1$HMR 400 MHz (CDCl$_3$) δ (ppm): 1.35 (6H, d, J=6.1 Hz, CH$_3$), 3.56 (3H, s, OCH$_3$), 4.07 (2H, broad s, NCH$_2$), 4.59 (1H, m, CH), 6.08 (1H, broad s, NH), 6.86–6.91 (2H, m, aromatics), 7.20–7.24 (2H, m, aromatics). The hydrochloride salt was obtained as a white solid: mp 90° C. Anal. calcd for C$_{11}$H$_{17}$NO$_2$—HCl: C, 57.02; H, 7.83; N, 6.04. Found: C, 56.93; H, 7.64; N, 5.96

Preparation of 2-(2,2-Dimethyl-5-oxo-[1,3]
dioxolan-4-ylidene)-N-(2-isopropoxy-benzyl)-N-methoxy-acetamide

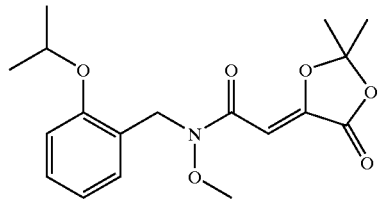

Reaction of (2,2-dimethyl-5-oxo-[1,3]dioxolan-4-ylidene)-acetyl chloride with N-(2-isopropoxy-benzyl)-O-methyl-hydroxylamine as described in the preparation of compound 1-C gave the title amide as white crystals (93% yield): mp 103° C. (ethyl acetate-hexane). $^1$HNMR 400 MHz (CDCl$_3$) δ (ppm): 1.34 (6H, d, J=6.0 Hz, CH$_3$), 1.75 (6H, s, CH$_3$), 3.68 (3H, s, OCH$_3$), 4.60 (1H, m, CH), 4.95 (2H, broad s, NCH$_2$), 6.44 (1H, s, CH), 6.89 (2H, m, aromatics), 7.2–7.3 (2H, m, aromatics). Anal. calcd for C$_{18}$H$_{23}$NO$_6$: C, 61.88; H, 6.64; N, 4.01. Found: C, 61.22; H, 6.33; N, 3.87.

EXAMPLE 23

3-Hydroxy-4-methanesulfonylamino-4-oxo-but-2-enoic acid (2-isopropoxy-benzyl)-methoxy-amide

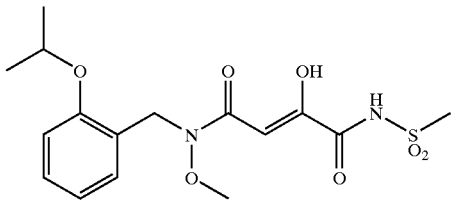

Reaction of 2-(2,2-dimethyl-5-oxo-[1,3]dioxolan-4-ylidene)-N-(2-isopropoxy-benzyl)-N-methoxy-acetamide (0.234 g, 0.67 mmol) with methanesulfonamide (0.064 g, 0.67 mmol) as described in the preparation of compound 22 gave 0.135 g (53% yield) of the title amide as a light yellow solid. $^1$H NMR (400 MHz, DMSO) δ: mixture of rotamers: 1.25 and 1.30 (2×3H, 2 d, J=6 Hz, CH$_3$), 2.86 and 2.88 (3H, 2 S, SO$_2$CH$_3$), 3.63 and 3.67 (3H, 2 s, OCH$_3$), 4.62 (1H, m, CH), 4.76 (2H, s, NCH$_2$), 6.19 and 6.23 (1H, 2 s, CH), 6.8–7.2 (4H, m, aromatics). HRMS (ESI/neg) calculated for C$_{16}$H$_{21}$N$_2$O$_7$S: [M−H]$^-$: 385.106948; found: 385.106655.

EXAMPLE 24

4-{[(3-Hydroxy-4-methanesulfonylamino-4-oxo-but-2-enoyl)-methoxy-amino]-methyl}-benzoic acid tert-butyl ester

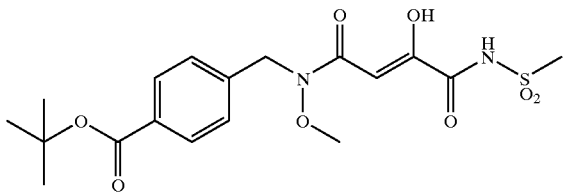

Reaction of 4-({[2-(2,2-dimethyl-5-oxo-[1,3]dioxolan-4-ylidene)-acetyl]-methoxy-amino}-methyl)-benzoic acid tert-butyl ester (0.060 g, 0.15 mmol) with methanesulfonamide (0.014 g, 0.15 mmol) as described in the prepartion of compound 22 gave 0.043 g (67% yield) of the title amide as a white solid. $^1$H NMR (400 MHz, CDCl$_3$) δ: mixture of rotamers: 1.58 (9H, s t-Bu), 3.31, 3.33 and 3.36 (3H, 3 S, SO$_2$CH$_3$), 3.61, 3.66 and 3.70 (3H, 3 s, OCH$_3$), 4.8 and 4.88 (2H, 2 s, NCH$_2$), 6.6 (1H, s, CH), 7.28 (2H, m, aromatics), 7.98 (2H, m, aromatics), 8.98 (1H, broad s, NH). HRMS (ESI/neg) calculated for C$_{18}$H$_{23}$N$_2$O$_8$S: [M−H]$^-$: 427.117513; found: 427.117342.

Preparation of 3-Fluoro-4-methyl-benzaldehyde O-methyl-oxime

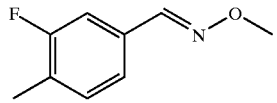

Reaction of 3-fluoro-4-methyl-benzaldehyde with methoxylamine hydrochloride as described in the preparation of compound 1-A gave the title oxime ether as a clear oil (94% yield). $^1$HMR indicated a 9:1 mixture of E- and Z-isomers. $^1$HNMR 400 MHz (CDCl$_3$) δ (ppm): (E-isomer) 2.28 (3H, broad s, CH$_3$), 3.97 (3H, s, OCH$_3$), 7.15–7.29 (3H, m, aromatics), 7.99 (1H, s, CH).

Preparation of N-(3-Fluoro-4-methyl-benzyl)-O-methyl-hydroxylamine

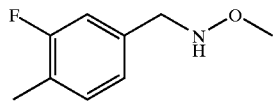

Reduction of 3-fluoro-4-methyl-benzaldehyde O-methyloxime with sodium cyanoborohydride as described in the preparation of compound 1-B gave the title hydroxylamine as a clear oil after chromatography on silica gel (elution hexane-ethyl acetate 8: 2) (57% yield). $^1$HNMR 400 MHz (CDCl$_3$) δ (ppm): 2.25 (3H, broad s, CH$_3$), 3.50 (3H, s, OCH$_3$), 3.99 (2H, broad s, NCH$_2$), 5.71 (1H, broad, NH), 7.01 (2H, m, aromatics), 7.13 (1H, m, aromatic). The hydrochloride salt was obtained as a white solid: mp 140–142° C. Anal. calcd for C$_9$H$_{12}$FNO—HCl: C, 52.56; H, 6.37; N, 6.81. Found: C, 52.63; H, 6.30; N, 6.78.

Preparation of 2-(2,2-Dimethyl-5-oxo-[1,3] dioxolan-4-ylidene)-N-(3-fluoro-4-methyl-benzyl)-N-methoxy-acetamide

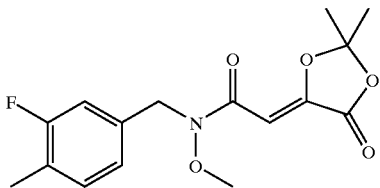

Reaction of (2,2-dimethyl-5-oxo-[1,3]dioxolan-4-ylidene)-acetyl chloride with N-(3-fluoro-4-methyl-benzyl)-O-methyl-hydroxylamine as described in the preparation of compound 1-C gave the title amide as white crystals (100% yield): mp 131° C. (ethyl acetate-hexane). $^1$HNMR 400 MHz (CDCl$_3$) δ (ppm): 1.75 (6H, s, CH$_3$), 2.25 (3H, broad s, CH$_3$), 3.69 (3H, s, OCH$_3$), 4.77 (2H, s, NCH$_2$), 6.39 (1H, s, CH), 7.0–7.03 (2H, m, aromatics), 7.13 (1H, m, aromatic). Anal. calcd for C$_{16}$H$_{18}$FNO$_5$: C, 59.43; H, 5.61; N, 4.33. Found: C, 59.51; H, 5.60; N, 4.24.

EXAMPLE 25

3-Hydroxy-4-methanesulfonylamino-4-oxo-but-2-enoic acid (3-fluoro-4-methyl-benzyl)-methoxy-amide

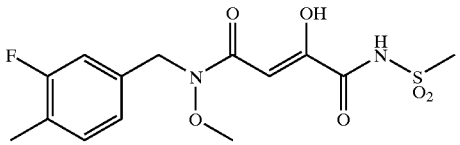

Reaction of 2-(2,2-dimethyl-5-oxo-[1,3]dioxolan-4-ylidene)-N-(3-fluoro-4-methyl-benzyl)-N-methoxy-acetamide (0.135 g, 0.418 mmol) with methanesulfonamide (0.042 g, 0.44 mmol) as described in the preparation of compound 22 gave 0.102 g (68% yield) of the title amide as a white solid. $^1$H NMR (400 MHz, DMSO) δ: mixture of rotamers: 2.2 (3H, s, CH$_3$), 2.87 and 2.88 (3H, 2 S, SO$_2$CH$_3$), 3.63 and 3.67 (3H, 2 s, OCH$_3$), 4.73 and 4.78 (2H, 2 s, NCH$_2$), 6.14 and 6.16 (1H, 2 s, CH), 7.04–7.27 (3H, m, aromatics). HRMS (ESI/neg) calculated for C$_{14}$H$_{16}$FN$_2$O$_6$S: [M–H]$^-$: 359.071312; found: 359.071347.

Preparation of 1-(4-Fluoro-phenyl)-ethanone O-methyl-oxime

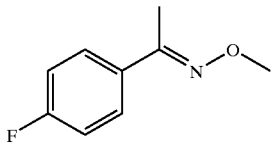

Reaction of 4'-fluoroacetophenone with methoxylamine hydrochloride as described in the preparation of compound 1-A gave the title oxime ether as a clear oil (92% yield). $^1$HNMR indicated a 87:13 mixture of E and Z isomers. $^1$HNMR 400 MHz (CDCl$_3$) δ (ppm): (E-isomer) 2.21 (3H, s, CH$_3$), 3.99 (3H, s, OCH$_3$), 7.04 (2H, m, aromatics), 7.63 (2H, m, aromatics).

Preparation of N-[1-(4-Fluoro-phenyl)-ethyl]-O-methyl-hydroxylamine

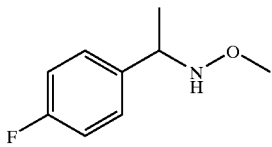

Reduction of 4'-fluoroacetophenone O-methyloxime with sodium cyanoborohydride as described in the preparation of 1-B gave the title hydroxylamine as a clear oil after chromatography on silica gel (elution hexane-ethyl acetate 8:2) (51% yield). $^1$HNMR 400 MHz (CDCl$_3$) δ (ppm): 1.33 (3H, d, J=6.5 Hz, CH$_3$), 3.46 (3H, s, OCH$_3$), 4.12 (1H, q, J=6.5 Hz, NCH), 5.59 (1H, broad, NH), 7.02 (2H, m, aromatics), 7.32 (2H, m, aromatics). The hydrochloride salt was obtained as a white solid: mp 99–103° C. Anal. calcd for C$_9$H$_{12}$FNO—HCl: C, 52.56; H, 6.37; N, 6.81. Found: C, 52.45; H, 6.25; N, 6.55.

Preparation of 2-(2,2-Dimethyl-5-oxo-[1,3]dioxolan-4-ylidene)-N-[1-(4-fluoro-phenyl)-ethyl]-N-methoxy-acetamide

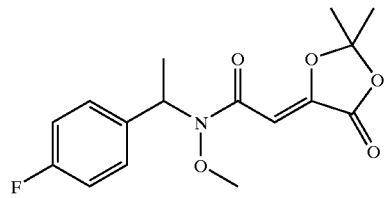

Reaction of (2,2-dimethyl-5-oxo-[1,3]dioxolan-4-ylidene)-acetyl chloride with N-[1-(R and S)-(4-fluoro-phenyl)-ethyl]-O-methyl-hydroxylamine as described in the preparation of compound 1-C gave the title amide as a clear syrup (100%). $^1$HNMR 400 MHz (CDCl$_3$) δ (ppm): 1.62 (3H, d, J=7.5 Hz, CH$_3$), 1.75 (6H, s, CH$_3$), 3.52 (3H, s, OCH$_3$), 5.72 (1H, q, J=7.5 Hz, CH), 6.31 (1H, s, CH), 7.02 (2H, m, aromatics), 7.41 (2H, m, aromatics). HRMS (MAB N$_2$) calculated for C$_{16}$H$_{18}$FNO$_5$ [M+]: 323.116901: found: 323.117106.

EXAMPLE 26

Preparation of 3-Hydroxy-4-methanesulfonylamino-4-oxo-but-2-enoic acid[1-(4-fluoro-phenyl)-ethyl]-methoxy-amide

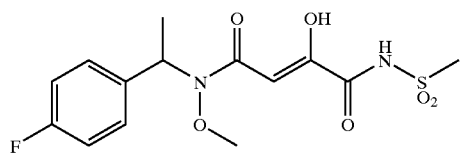

Reaction of 2-(2,2-dimethyl-5-oxo-[1,3]dioxolan-4-ylidene)-N-[1-(R and S)-(4-fluoro-phenyl)-ethyl]-N-methoxy-acetamide (0.160 g, 0.49 mmol) with methanesulfonamide (0.050 g, 0.52 mmol) as described in the preparation of compound 22 gave 0.091 g (51% yield) of the title amide as a white solid. $^1$H NMR (400 MHz, DMSO) δ: mixture of rotamers: 1.55 (3H, m, CH$_3$), 2.77, 2.78, 2.86 and 2.88 (3H, 4 s, SO$_2$CH$_3$), 3.44, 3.53 and 3.58 (3H, 3 s, OCH$_3$), 5.47–5.7 (1H, m, NCH), 6.09, 6.10, 6.11 and 6.12 (1H, 4 s, CH), 7.12–7.43 (4H, m, aromatics). HRMS (ESI/neg) calculated for C$_{14}$H$_{16}$FN$_2$O$_6$S: [M–H]$^-$: 359.071312; found: 359.071165.

Preparation of Bis-(4-fluoro-phenyl)-methanone O-methyl-oxime

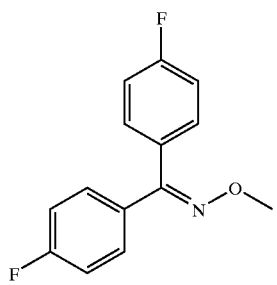

A solution of 4,4'-difluorobenzophenone (3.00 g, 13.75 mmol) in a mixture of ethanol (10 ml) and pyridine (10 ml)

was treated with methoxyamine hydrochloride (1.8 g, 21.7 mmol) and the resulting mixture was heated under reflux for 1 h. The cooled reaction mixture was diluted with ethyl acetate, washed successively with water, 1 N hydrochloric acid, saturated sodium bicarbonate and brine. After drying over anhydrous magnesium sulphate, evaporation of the solvent yielded 3.38 g (99% yield) of the title oxime ether as a clear syrup. $^1$HNMR 400 MHz (CDCl$_3$) δ (ppm): 3.94 (3H, s, OCH$_3$), 7.04 (2H, m, aromatics), 7.12 (2H, m, aromatics), 7.34 (2H, m, aromatics), 7.45 (2H, m, aromatics).

Preparation of N-[Bis-(4-fluoro-phenyl)-methyl]-O-methyl-hydroxylamine

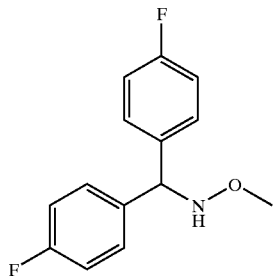

Reduction of 4,4'-difluorobenzophenone O-methyloxime with sodium cyanoborohydride as described in the preparation of 1-B gave the title hydroxylamine as a clear oil after chromatography on silica gel (elution hexane-dichloromethane 1:1) (41% yield). $^1$HNMR 400 MHz (CDCl$_3$) δ (ppm): 3.49 (3H, s, OCH$_3$), 5.18 (1H, s, NCH), 5.8 (1H, broad, NH), 7.02 (4H, m, aromatics), 7.35 (4H, m, aromatics). The hydrochloride salt was obtained as a white solid: mp 162° C. (dec). Anal. calcd for C$_{14}$H$_{13}$F$_2$NO—HCl: C, 58.85; H, 4.94; N, 4.90. Found: C, 59.05; H, 4.74; N, 4.77.

Preparation of N-[Bis-(4-fluoro-phenyl)-methyl]-2-(2,2-dimethyl-5-oxo-[1,3]dioxolan-4-ylidene)-N-methoxy-acetamide

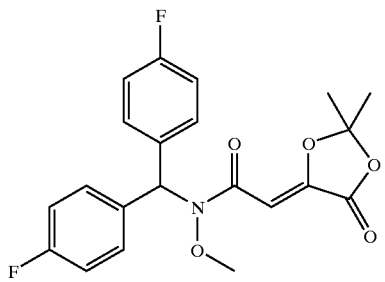

Reaction of (2,2-dimethyl-5-oxo-[1,3]dioxolan-4-ylidene)-acetyl chloride with N-[bis-(4-fluoro-phenyl)-methyl]-O-methyl-hydroxylamine as described in the preparation of compound 1-C gave the title amide as white crystals (88% yield): mp 137° C. (ethyl acetate-hexane). $^1$HNMR 400 MHz (CDCl$_3$) δ (ppm): 1.74 (6H, s, CH$_3$), 3.26 (3H, s, OCH$_3$), 6.42 (1H, s, CH), 6.81 (1H, s, CH), 7.03 (4H, m, aromatics), 7.28 (4H, m, aromatics). Anal. calcd for C$_{21}$H$_{19}$F$_2$NO$_5$: C, 62.53; H, 4.75; N, 3.47. Found: C, 62.49; H, 4.66; N, 3.35.

EXAMPLE 27

3-Hydroxy-4-methanesulfonylamino-4-oxo-but-2-enoic acid [bis-(4-fluoro-phenyl)-methyl]-methoxy-amide

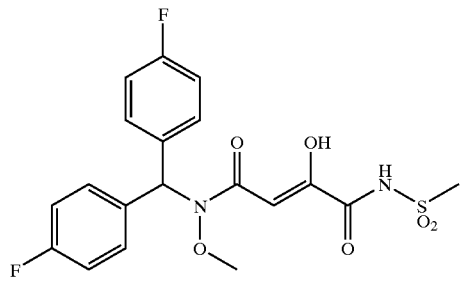

A solution of N-[bis-(4-fluoro-phenyl)-methyl]-2-(2,2-dimethyl-5-oxo-[1,3]dioxolan-4-ylidene)-N-methoxy-acetamide (0.175 g, 0.43 mmol) and methanesulfonamide (0.062 g, 0.52 mmol) in anhydrous N,N-dimethylformamide (3 ml) was treated at 25° C. with 1,8-diazabicyclo[5.4.0]undec-7-ene (0.1 ml). After 1 h, the reaction mixture was then quenched by the addition of ethyl acetate and 1 N hydrochloric acid. The organic phase was washed successively with water and brine and dried over anhydrous magnesium sulfate. Evaporation of the solvent and chromatography of the residue on silica gel (elution ethyl acetate-methanol 0–20%) gave 0.129 g (67% yield) of the title amide as a white solid. $^1$H NMR (400 MHz, DMSO) δ: mixture of rotamers: 2.78, 2.81, 2.87 and 2.88 (3H, 4 s, SO$_2$CH$_3$), 3.15, 3.16, 3.18 and 3.20 (3H, 4 s, OCH$_3$), 6.22, 6.25 and 6.27 (1H, 3 s, CH), 6.75–6.89 (1H, m, CH), 7.17–7.54 (8H, m, aromatics). HRMS (ESI/neg) calculated for C$_{19}$H$_{17}$F$_2$N$_2$O$_6$S, [M–H]$^-$: 439.077540; found: 439.077728.

2-Chloro-4-fluoro-benzaldehyde O-methyl-oxime

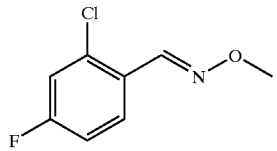

Reaction of 2-chloro-4-fluoro-benzaldehyde with methoxylamine hydrochloride as described in the preparation of compound 1-A gave the title oxime ether as a clear oil (93% yield). $^1$HNMR indicated a 9:1 mixture of E- and Z-isomers. $^1$HNMR 400 MHz (CDCl$_3$) δ (ppm): (E-isomer) 3.99 (3H, s, OCH$_3$), 6.99 (1H, m, aromatic), 7.12 (1H, m, aromatic), 7.87 (1H, m, aromatic), 8.41 (1H, s, CH).

Preparation of N-(2-Chloro-4-fluoro-benzyl)-O-methyl-hydroxylamine

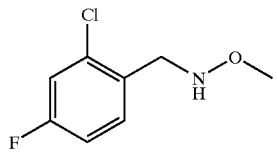

Reduction of 2-chloro-4-fluoro-benzaldehyde O-methyloxime with sodium cyanoborohydride as described in the preparation of 1-B gave the title hydroxylamine as a clear oil after chromatography on silica gel (elution dichloromethane-ethyl acetate 95:5) (54% yield). $^1$HNMR 400 MHz (CDCl$_3$) δ (ppm): 3.55 (3H, s, OCH$_3$), 4.16 (2H, s, NCH$_2$), 6.99 (1H, m, aromatic), 7.15 (1H, dd, J=2.5 Hz and J=8.6 Hz, aromatic), 7.41 (1H, dd, J=6.0 Hz and J=8.6 Hz, aromatic). The hydrochloride salt was obtained as a white solid: mp 159° C. Anal. calcd for C$_8$H$_9$ClFNO—HCl: C, 42.50; H, 4.46; N, 6.20. Found: C, 42.50; H, 4.36; N, 5.98.

Preparation of N-(2-Chloro-4-fluoro-benzyl)-2-(2,2-dimethyl-5-oxo-[1,3]dioxolan-4-ylidene)-N-methoxy-acetamide

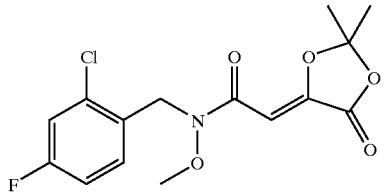

Reaction of (2,2-dimethyl-5-oxo-[1,3]dioxolan-4-ylidene)-acetyl chloride with N-(2-chloro-4-fluoro-benzyl)-O-methyl-hydroxylamine as described in the preparation of compound 1-C gave the title amide as white crystals (97% yield): mp 127–128° C. (ethyl acetate-hexane). $^1$HNMR 400 MHz (CDCl$_3$) δ (ppm): 1.76 (6H, s, CH$_3$), 3.70 (3H, s, OCH$_3$), 4.95 (2H, s, NCH$_2$), 6.41 (1H, s, CH), 6.96 (1H, m, aromatic), 7.13 (1H, dd, J=2.5 Hz and J=8.7 Hz, aromatic), 7.38 (1H, dd, J=6.1 Hz and J=8.6 Hz, aromatic). Anal. calcd for C$_{15}$H$_{15}$ClFNO$_5$: C, 52.41; H, 4.39; N, 4.07. Found: C, 52.49; H, 4.15; N, 3.76.

EXAMPLE 28

3-Hydroxy-4-methanesulfonylamino-4-oxo-but-2-enoic acid (2-chloro-4-fluoro-benzyl)-methoxy-amide

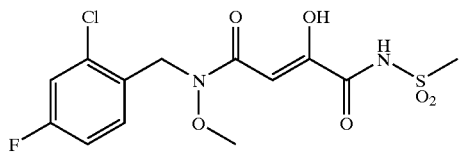

Reaction of N-(2-chloro-4-fluoro-benzyl)-2-(2,2-dimethyl-5-oxo-[1,3]dioxolan-4-ylidene)-N-methoxy-acetamide (0.175 g, 0.51 mmol) with methanesulfonamide (0.073 g, 0.77 mmol) as described in the preparation of compound 22 gave 0.089 g (45% yield) of the title amide as a white solid after crystallization from ethyl acetate-hexane; mp=144° C. (decomposition). $^1$H NMR (400 MHz, CDCl$_3$) δ: 3.36 (3H, s, SO$_2$CH$_3$), 3.71 (3H, s, OCH$_3$), 4.96 (2H, s, NCH$_2$), 6.60 (1H, s, CH), 6.95–7.32 (3H, m, aromatics), 8.96 (1H, broad s, NH). Anal. calcd for C$_{13}$H$_{14}$ClFN$_2$O$_6$S: C, 41.00; H, 3.70; N, 7.35; found: C, 41.03; H, 3.61; N, 7.29.

Preparation of [1-(4-Chloro-benzyl)-2-(4-chloro-phenyl)-ethyl]-methyl-amine

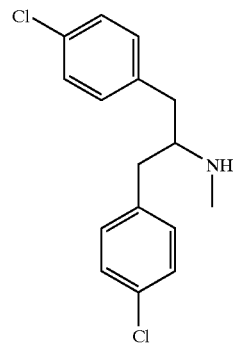

A mixture of 1,3-bis-(4-chlorophenyl)-propan-2-one (3.20 g, 11.46 mmol), (Yang, H. and Hay, A. S., Synthesis, 1992, 467–472), in anhydrous ethanol (25 ml) was treated successively with titanium (IV) isopropoxide (6.8 ml, 22.9 mmol), methylamine hydrochloride (1.55 g, 22.9 mmol) and triethylamine (3.2 ml, 22.9 mmol). The resulting mixture was stirred at 22° C. for 18 h and then treated with sodium borohydride (0.65 g, 17.2 mmol). After 6 h at 22° C., the reaction mixture was quenched by the addition of 2 N aqueous ammonia (60 ml) and the resulting precipitate was filtered and rinced with ether. The combined ether extracts were washed with brine, dried (anhydrous sodium carbonate) and concentrated. Distillation of the residue in vacuo gave 2.60 g (77% yield) of the title amine as a clear oil: bp 135–140° C./0.2 torr, (bulb to bulb distillation, air bath temperature). $^1$HNMR 400 MHz (C$_6$D$_6$) δ (ppm): 2.19 (3H, s, NCH3), 2.42 (4H, d, J=6.5 Hz, CH$_2$), 2.69 (1H, m, CH), 6.84 (4H, d, J=8.5 Hz, aromatics), 7.22 (4H, d, J=8.5 Hz, aromatics). The hydrochloride salt was obtained as a white solid. Anal. calcd for C$_{16}$H$_{17}$C$_2$N—HCl: C, 58.11; H, 5.49; N, 4.24. Found: C, 57.85; H, 5.35; N, 4.13.

Preparation of N-[1-(4-Chloro-benzyl)-2-(4-chloro-phenyl)-ethyl]-2-(2,2-dimethyl-5-oxo-[1,3]dioxolan-4-ylidene)-N-methyl-acetamide

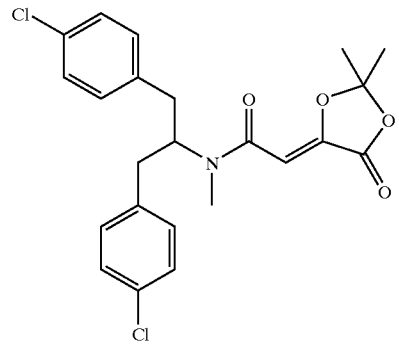

A mixture of (2,2-dimethyl-5-oxo-[1,3]dioxolan-4-ylidene)-acetic acid (0.936 g, 5.43 mmol) in dry acetonitrile (10 ml) was treated successively with [1-(4-chlorobenzyl)-2-(4-chlorophenyl)-ethyl]-methylamine (1.60 g, 5.43 mmol), benzotriazole-1-yl-oxy-tris-pyrrolidino-phosphonium hexafluorophosphate (PyBOP®) (3.11 g, 5.98 mmol) and triethylamine (0.83 ml, 5.98 mmol). After 3 h at 22° C., the clear solution was diluted with ethyl acetate, washed with 0.1 N hydrochloric acid, saturated sodium bicarbonate, brine and dried (magnesium sulfate). Evaporation of the solvent and chromatography of the residue on silica gel (elution toluene-ethyl acetate, 7:3) gave 2.35 g (97% yield) of the title amide as white needles; mp 109° C. (ethyl acetate-hexane). ¹HNMR 400 MHz (CDCl₃) δ (ppm): mixture of rotamers; 1.62 and 1.69 (6H, 2 s, CH₃), 2.75 and 2.97 (3H, 2 s, NCH₃), 2.8–2.9 (4H, m, CH₂), 4.15 (1H, m, CH), 5.44 and 5.89 (1H, 2 s, CH), 7.05–7.3 (8H, m, aromatics). Anal. calcd for C₂₃H₂₃C₁₂NO₄: C, 61.62; H, 5.17; N, 3.12. Found: C, 61.39; H, 5.25; N, 3.22.

EXAMPLE 29

3-Hydroxy-4-methanesulfonylamino-4-oxo-but-2-enoic acid [1-(4-chloro-benzyl)-2-(4-chloro-phenyl)-ethyl]-methyl-amide

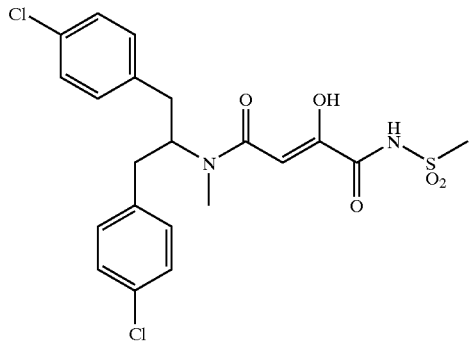

Reaction of N-[1-(4-chlorobenzyl)-2-(4-chlorophenyl)-ethyl]-2-(2,2-dimethyl-5-oxo-[1,3]dioxolan-4-ylidene)-N-methyl-acetamide (0.363 g, 0.81 mmol) with methanesulfonamide (0.077 g, 0.81 mmol) as described in the preparation of compound 22 gave 0.284 g (72% yield) of the title amide as a white solid. ¹H NMR (400 MHz, DMSO) δ: mixture of rotamers: 2.5–3.5 (10H, m, CH₃ and CH₂), 4.55 and 5.1 (1H, broad m, CH), 5.8 (1H, s, CH), 7.1–7.4 (8H, m, aromatics).

Preparation of 3-(4-Fluorophenyl)-propionaldehyde O-methyloxime

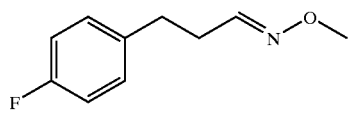

Reaction of 3-(4-fluorophenyl)-propionaldehyde (Dickinson, R. P.; Dack, K. N.; Steele, J.; Tute, M. S. Bioorg. Med. Chem. Lett., 6, 14, 1996, 1691–1696) with methoxy-lamine hydrochloride as described in the preparation of compound 1-A gave the title oxime ether as a clear oil (97% yield), bp 65–75° C./1.5 torr (bulb to bulb distillation, air bath temperature). ¹HNMR indicated a 6:4 mixture of E- and Z-isomers. ¹HNMR 400 MHz (CDCl₃) δ (ppm): 2.51 and 2.65 (2H, 2 m, CH₂), 2.8 (2H, m, CH₂), 3.84 and 3.88 (3H, 2 s, OCH₃), 6.67 (t, J=5.5 Hz, CH), 7.0 (2H, m, aromatics), 7.16 (2H, m, aromatics), 7.40 (t, J=4.2 Hz, CH).

Preparation of N-[3-(4-Fluorophenyl)-propyl]-O-methyl-hydroxylamine

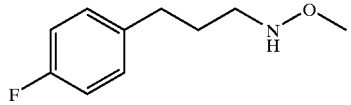

Reduction of 3-(4-fluorophenyl)-propionaldehyde O-methyloxime with sodium cyanoborohydride as described in the preparation of compound 1-B gave the title hydroxy-lamine as a clear oil after chromatography on silica gel and distillation in vacuo (75% yield): bp 70–75° C./0.7 torr (bulb to bulb distillation, air bath temperature). ¹HNMR 400 MHz (CHCl₃) δ (ppm): 1.85 (2H, m, CH₂), 2.68 (2H, t, J=7.9 Hz, CH₂), 2.95 (2H, t, J=7.1 Hz, CH₂), 3.56 (3H, s, OCH₃), 5.58 (1H, broad, NH), 6.99 (2H, m, aromatics), 7.17 (2H, m, aromatics). The hydrochloride salt was obtained as a white solid: mp 97–100° C. Anal. calcd for C₁₀H₁₄FNO—HCl: C, 54.67; H, 6.88; N, 6.38. Found: C, 54.72; H, 6.71; N, 6.42.

Preparation of 2-(2,2-Dimethyl-5-oxo-[1,3]dioxolan-4-ylidene)-N-[3-(4-fluoro-phenyl)-propyl]-N-methoxy-acetamide

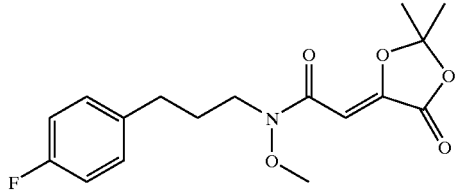

Reaction of (2,2-dimethyl-5-oxo-[1,3]dioxolan-4-ylidene)-acetyl chloride with N-[3-(4-fluorophenyl)-propyl]-O-methyl-hydroxylamine as described in the preparation of compound 1-C gave the title amide as white crystals (97% yield): mp 90–91° C. (ethyl acetate-hexane). ¹HNMR 400 MHz (CDCl₃) δ (ppm): 1.77 (6H, s, CH₃), 1.98 (2H, m, CH₂), 2.64 (2H, t, J=7.9 Hz, CH₂), 3.71 (2H, t, J=7.6 Hz, NCH₂), 3.73 (3H, s, OCH₃), 6.41 (1H, broad s, CH), 6.98 (2H, m, aromatics), 7.16 (2H, m, aromatics). Anal. calcd for C₁₇H₂₀FNO₅: C, 60.53; H, 5.98; N, 4.15. Found: C, 60.43; H, 5.99; N, 4.09.

EXAMPLE 30

3-Hydroxy-4-methanesulfonylamino-4-oxo-but-2-enoic acid [3-(4-fluoro-phenyl)-propyl]-methoxy-amide

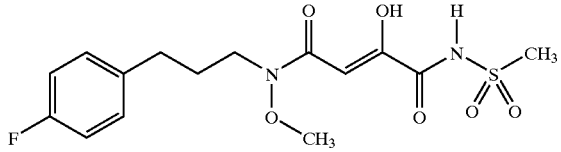

Reaction of 2-(2,2-dimethyl-5-oxo-[1,3]dioxolan-4-ylidene)-N-[3-(4-fluorophenyl)-propyl]-N-methoxy-acetamide (0.300 g, 0.89 mmol) with methanesulfonamide (0.127 g, 1.33 mmol) as described in the preparation oc compound 22 gave 0.304 g (91% yield) of the title amide as a white foam after chromatography. ¹H NMR (400 MHz, CDCl₃) δ: mixture keto-enol forms and of rotamers equilibrating to a major enol form after a few hours in chloroform:

1.95 (2H, m, $CH_2$), 2.6 (2H, m, $CH_2$), 3.34, 3.35 and 3.38 (3H, 3s, $SO_2CH_3$), 3.70, 3.71 and 3.74 (3H, 3s, $OCH_3$), 6.57 (1H, s, CH), 7.0 (2H, m, aromatics), 7.15 (2H, m, aromatics), 9.05 (1H, broad s, NH); major form after equilibration: 1.97 (2H, m, $CH_2$), 2.64 (2H, t, $CH_2$), 3.38 (3H, s, $SO_2CH_3$), 3.74 (3H, s, $OCH_3$), 6.57 (1H, s, CH), 7.0 (2H, m, aromatics), 7.15 (2H, m, aromatics), 9.05 (1H, broad s, NH). MS (ESI/pos) calculated for $C_{15}H_{20}FN_2O_6S$, $[M+H]^+$: 374; found: 374.

EXAMPLE 31

HIV-Integrase Inhibition Activity

Table 2 shows the percent inhibition of HIV-integrase in the presence of examples 1–30 at 10 μM. For each reaction, 5 pmole of biotin labeled substrate DNA was bound to 100 ug of Streptavidin coated PVT SPA beads (Amersham Pharmacia Biotech). 0.26 ng of recombinant integrase was incubated with the beads for 90 min at 37 C. Unbound enzyme was removed by washing the complex followed by addition of inhibitors and 0.1 fmol of P33 labeled target DNA. Reaction was stopped by adding EDTA to a final concentration of 10 mM. Samples were counted in Top-CountNXT (Packard) and the CPM was used as a measure of integration. Reaction condition was as described in A. Engelman and R. Craigie, J. Virol. 69, 5908–5911 (1995). The sequences of substrate and target DNA were described in Nucleic Acid Research 22, 1121–1122 (1994). Compounds of this invention tested in this assay have $IC_{50}$'s of approximately 0.01 to 25 μM.

TABLE 2

| Example | % inhibition at 10 μM |
|---|---|
| 1 | 99 |
| 2 | 99 |
| 3 | 99 |
| 4 | 99 |
| 5 | 99 |
| 6 | 99 |
| 7 | 99 |
| 8 | 99 |
| 9 | 94 |
| 10 | 95 |
| 11 | 99 |
| 12 | 99 |
| 13 | 98 |
| 14 | 93 |
| 15 | 93 |
| 16 | 98 |
| 17 | 99 |
| 18 | 99 |
| 19 | 99 |
| 20 | 99 |
| 21 | 30 |
| 22 | 99 |
| 23 | 99 |
| 24 | 15 |
| 25 | 99 |
| 26 | 99 |
| 27 | 60 |
| 28 | 99 |
| 29 | 86 |
| 30 | 98 |

Inhibition of HIV Replication

Cell culture assays were performed using a single cycle, recombinant HIV virus expressing Renella luciferase. Antiviral activity was evaluated by measuring the production of luciferase in the infected cells 5 days post-infection. Susceptibility of the virus to compounds was determined by incubation in the presence of the serially-diluted compound. The 50% effective concentration ($EC_{50}$) was calculated by using the exponential form of the median effect equation where $(Fa)=1/[1+(ED_{50}/\text{drug conc.})^m]$. Compounds of this invention tested in this assay have $EC_{50}$'s of approximately 0.08 to 12 μM.

What is claimed:

1. A compound of Formula I, or pharmaceutically acceptable salt, or solvate thereof

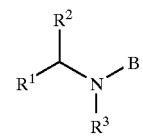

Formula I wherein:
$R^1$ is
-phenyl, or
—$C_1$–$C_6$ alkyl-phenyl;
wherein phenyl is unsubstituted or substituted with 1–3 $R^4$;
$R^2$ is
—H,
—$C_1$–$C_6$ alkyl,
-phenyl, or
—$C_1$–$C_6$ alkyl phenyl;
wherein phenyl is unsubstituted or substituted with 1–3 $R^4$;
$R^3$ is
—H,
—$C_1$–$C_6$ alkyl, or
—O—$C_1$–$C_6$ alkyl;
Each $R^4$ is independently selected from
-halo,
—$C_1$–$C_6$ alkyl,
—$C_1$–$C_6$ haloalkyl,
—$OR^5$, and
—$CO_2R^5$;
Each $R^5$ is independently selected from
—H and
—$C_1$–$C_6$ alkyl;
B is selected from the group consisting of

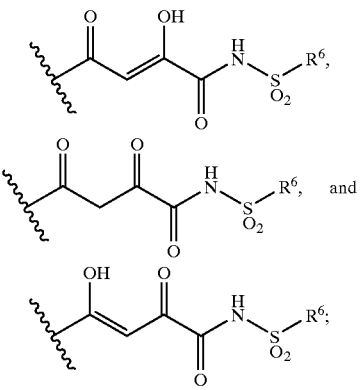

$R^6$ is
—$C_1$–$C_6$ alkyl;
—$C_3$–$C_7$ cycloalkyl;
1-($C_1$–$C_3$)alkylcyclopropyl;
1-benzylcyclopropyl;
-tetrahydrothiophene 1,1-dioxoide;

-phenyl, unsubstituted or substituted with 1–2 substituents selected from halo, —$C_1$–$C_6$ alkyl, —$C_1$–$C_6$ alkoxy, —$C_1$–$C_6$ carboalkoxy, —$C_1$–$C_6$ alkylamido, and N-[[(1-ethyl)pyrrolidin-2-yl]methyl] carboxamido; or -heteroaryl selected from the group consisting of thienyl, furanyl, pyrrolyl, pyridinyl, oxadiazolyl, thiadiazolyl, isoxazolyl, imidazolyl, oxathiazolyl, oxathiazolyl, benzofuranyl, indolyl, benzoxazolyl, benzthiazolyl, thienyl, and pyrazolylthienyl moieties unsubstituted or substituted with 1–2 substituents selected from halo, —$C_1$–$C_6$ alkyl, —$C_1$–$C_2$ perhaloalkyl, —$C_1$–$C_6$ alkoxy, —$C_1$–$C_6$ carboalkoxy, and —$C_1$–$C_6$ alkylamido.

2. A compound of claim 1 wherein $R^1$ is phenyl substituted with 1–3 $R^4$ and $R^2$ is hydrogen.

3. A compound of claim 1 wherein $R^1$ is —$(CH_2)_2$-phenyl where phenyl is substituted with 1–3 $R^4$, and $R^2$ is hydrogen.

4. A compound of claim 1 wherein $R^6$ is —$C_1$–$C_6$ alkyl or —$C_3$–$C_7$ cycloalkyl.

5. A compound of claim 1 wherein $R^6$ is phenyl, unsubstituted or substituted with 1–2 substituents selected from halo, —$C_1$–$C_6$ alkyl, —$C_1$–$C_6$ alkoxy, —$C_1$–$C_6$ carboalkoxy, —$C_1$–$C_6$ alkylamido, and N-[[(1-ethyl) pyrrolidin-2-yl]methyl]carboxamido.

6. A compound of claim 1 wherein $R^6$ is heteroaryl selected from the group consisting of thienyl, furanyl, pyrrolyl, pyridinyl, pyrimidinyl, pyridazinyl, oxadiazolyl, thiadiazolyl, isoxazolyl, imidazolyl, oxathiazolyl, oxathiazolyl, benzofuranyl, indolyl, benzoxazolyl, benzthiazolyl, thienyl, and pyrazolylthienyl moieties unsubstituted or substituted with 1–2 substituents selected from halo, —$C_1$–$C_6$ alkyl, —$C_1$–$C_2$ perhaloalkyl, —$C_1$–$C_6$ alkoxy, —$C_1$–$C_6$ carboalkoxy, and —$C_1$–$C_6$ alkylamido.

7. A compound of claim 6 wherein $R^6$ is heteroaryl selected from the group consisting of 2-chlorothien-5-yl; 2-methylpyridin-6-yl; 2-acetamido-1,3,4-thiadiazol-5-yl; 3,5-dimethylisoxazol-4-yl; 1-methylimidazol-4-yl; 2,4-dimethyloxathiazol-5-yl; 6-ethoxybenzthiazol-2-yl; and 2-(1-methyl-5-trifluoromethyl-1H-pyrazol-3-yl)-thien-5-yl.

8. A compound of claim 1 selected from the group consisting of

3-Hydroxy-4-oxo-4-(toluene-4-sulfonylamino)-but-2-enoic acid (4-fluoro-benzyl)-methoxy-amide;

3-Hydroxy-4-methanesulfonylamino-4-oxo-but-2-enoic acid (4-fluoro-benzyl)-methoxy-amide;

4-(5-Acetylamino-[1,3,4]thiadiazole-2-sulfonylamino)-3-hydroxy-4-oxo-but-2-enoic acid (4-fluoro-benzyl)-methoxy-amide;

4-Cyclobutylmethanesulfonylamino-3-hydroxy-4-oxo-but-2-enoic acid (4-fluoro-benzyl)-methoxy-amide;

4-Cyclohexanesulfonylamino-3-hydroxy-4-oxo-but-2-enoic acid (4-fluoro-benzyl)-methoxy-amide;

4-Cyclopentanesulfonylamino-3-hydroxy-4-oxo-but-2-enoic acid (4-fluoro-benzyl)-methoxy-amide;

4-Cyclopropanesulfonylamino-3-hydroxy-4-oxo-but-2-enoic acid (4-fluoro-benzyl)-methoxy-amide;

4-(3,5-Dimethyl-isoxazole-4-sulfonylamino)-3-hydroxy-4-oxo-but-2-enoic acid (4-fluoro-benzyl)-methoxy-amide;

3-Hydroxy-4-(6-methyl-pyridine-2-sulfonylamino)-4-oxo-but-2-enoic acid (4-fluoro-benzyl)-methoxy-amide;

4-(5-Chloro-thiophene-2-sulfonylamino)-3-hydroxy-4-oxo-but-2-enoic acid (4-fluoro-benzyl)-methoxy-amide;

4-(4-Acetylamino-benzenesulfonylamino)-3-hydroxy-4-oxo-but-2-enoic acid (4-fluoro-benzyl)-methoxy-amide;

4-(6-Ethoxy-benzothiazole-2-sulfonylamino)-3-hydroxy-4-oxo-but-2-enoic acid (4-fluoro-benzyl)-methoxy-amide;

4-(2,4-Dimethyl-thiazole-5-sulfonylamino)-3-hydroxy-4-oxo-but-2-enoic acid (4-fluoro-benzyl)-methoxy-amide;

3-Hydroxy-4-(1-methyl-1H-imidazole-4-sulfonylamino)-4-oxo-but-2-enoic acid (4-fluoro-benzyl)-methoxy-amide;

N-(1-Ethyl-pyrrolidin-2-ylmethyl)-5-[3-[(4-fluoro-benzyl)-methoxy-carbamoyl]-2-hydroxy-acryloylsulfamoyl]-2-methoxy-benzamide;

4-(1,1-Dioxo-tetrahydro-1$\lambda^6$-thiophene-3-sulfonylamino)-3-hydroxy-4-oxo-but-2-enoic acid (4-fluoro-benzyl)-methoxy-amide;

3-Hydroxy-4-[5-(1-methyl-5-trifluoromethyl-1H-pyrazol-3-yl)-thiophene-2-sulfonylamino]-4-oxo-but-2-enoic acid (4-fluoro-benzyl)-methoxy-amide;

3-Hydroxy-4-oxo-4-(1-propyl-cyclopropanesulfonylamino)-but-2-enoic acid (4-fluoro-benzyl)-methoxy-amide;

4-(1-Cyclopropylmethyl-cyclopropanesulfonylamino)-3-hydroxy-4-oxo-but-2-enoic acid (4-fluoro-benzyl)-methoxy-amide;

4-(1-Benzyl-cyclopropanesulfonylamino)-3-hydroxy-4-oxo-but-2-enoic acid (4-fluoro-benzyl)-methoxy-amide;

3-Hydroxy-4-methanesulfonylamino-4-oxo-but-2-enoic acid (4-fluoro-3-methyl-benzyl)-methoxy-amide;

3-Hydroxy-4-methanesulfonylamino-4-oxo-but-2-enoic acid (2-isopropoxy-benzyl)-methoxy-amide;

3-Hydroxy-4-methanesulfonylamino-4-oxo-but-2-enoic acid (3-fluoro-4-methyl-benzyl)-methoxy-amide;

3-Hydroxy-4-methanesulfonylamino-4-oxo-but-2-enoic acid[1-(4-fluoro-phenyl)-ethyl]-methoxy-amide;

3-Hydroxy-4-methanesulfonylamino-4-oxo-but-2-enoic acid (2-chloro-4-fluoro-benzyl)-methoxy-amide;

3-Hydroxy-4-methanesulfonylamino-4-oxo-but-2-enoic acid [1-(4-chloro-benzyl)-2-(4-chloro-phenyl)-ethyl]-methyl-amide; and 3-Hydroxy-4-methanesulfonylamino-4-oxo-but-2-enoic acid [3-(4-fluoro-phenyl)-propyl]-methoxy-amide.

9. A composition useful for treating HIV infections comprising a therapeutic amount of a compound of claim 1 and a pharmaceutically acceptable carrier.

10. A method of inhibiting HIV integrase comprising contacting a compound of claim 1 with HIV integrase.

11. A method of inhibiting HIV viral DNA integration into human DNA comprising administering an effective amount of a compound of claim 1 to a cell infected with HIV.

12. A method for treating HIV infection in a patient in need thereof, comprising the administration of a therapeutically effective amount of a compound of claim 1, or a pharmaceutically acceptable salt or solvate thereof.

13. The method of claim 12, further comprising a therapeutically effective amount of one or more other HIV treatment agents selected from the following:

(a) an HIV protease inhibitor, (b) a nucleoside reverse transcriptase inhibitor, (c) a non-nucleoside reverse transcriptase inhibitor, (d) an HIV-entry inhibitor, (e) an immunomodulator, (f) or a combination thereof.

* * * * *